(12) United States Patent
Shibutani

(10) Patent No.: US 7,071,187 B2
(45) Date of Patent: Jul. 4, 2006

(54) NAPHTHYRIDINE DERIVATIVES

(75) Inventor: Tadao Shibutani, Naruto (JP)

(73) Assignee: Otsuka Pharmaceutical Factory, Inc., Tokushima (JP)

( * ) Notice: Subject to any disclaimer, the term of this patent is extended or adjusted under 35 U.S.C. 154(b) by 21 days.

(21) Appl. No.: 10/487,209

(22) PCT Filed: Feb. 21, 2002

(86) PCT No.: PCT/JP02/01520

§ 371 (c)(1),
(2), (4) Date: Feb. 18, 2004

(87) PCT Pub. No.: WO03/018580

PCT Pub. Date: Mar. 6, 2003

(65) Prior Publication Data

US 2004/0214853 A1    Oct. 28, 2004

(30) Foreign Application Priority Data

Aug. 23, 2001 (JP) ............................. 2001-252565

(51) Int. Cl.
*A61K 31/535* (2006.01)
*C07D 417/00* (2006.01)
*C07D 471/02* (2006.01)

(52) U.S. Cl. ..................... 514/228.2; 514/300; 544/61; 544/228.2; 546/122; 546/123

(58) Field of Classification Search ............. 544/228.2, 544/61; 514/300, 228.2; 546/122, 123
See application file for complete search history.

(56) References Cited

U.S. PATENT DOCUMENTS 6,245,779 B1    6/2001    Shibutani et al.

FOREIGN PATENT DOCUMENTS

| JP | 05/017475 | 1/1993 | | |
|---|---|---|---|---|
| JP | 07/010875 | 1/1995 | | |
| JP | 07/002779 | 2/1995 | | |
| JP | 07/304775 | 11/1995 | | |
| JP | 2003081946 | * | 3/2003 | ................. 546/123 |
| WO | WO 99/02527 | 1/1999 | | |

* cited by examiner

Primary Examiner—Cecilia J. Tsang
Assistant Examiner—Raymond Covington
(74) Attorney, Agent, or Firm—Sughrue Mion, PLLC

(57) ABSTRACT

The present invention provides a novel naphthyridine derivative that is effective for relieving pain, less toxic, and also is effective for treating diabetic neuropathy, the derivative being represented by the general formula (1):

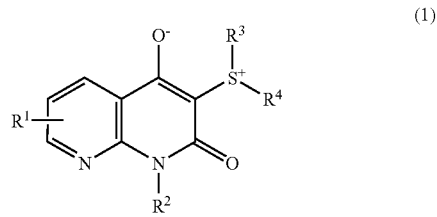

(1)

wherein $R^1$, $R^2$, $R^3$ and $R^4$ are as described in the description.

18 Claims, No Drawings

NAPHTHYRIDINE DERIVATIVES

This Application is a 371 of PCT/JP02/01520, filed Feb. 21, 2002, the disclosure of which is incorporated herein by reference.

TECHNICAL FIELD

The present invention relates to novel naphthyridine derivatives.

BACKGROUND ART

The inventor previously found novel naphthyridine derivatives that have an analgesic effect, and accomplished an invention relating to the derivatives [PCT/JP98/03045 (international publication No. WO 99/02527A1)]. However, in continued research, the inventor found that the derivatives show little effect in the case of treating diseases, such as diabetic neuropathy, in which the nervous system is damaged, barely achieving the desired analgesic effect, and furthermore, the inventor recognized that administration of the derivatives may cause side effects, such as hypertrophy of the thyroid gland, etc.

DISCLOSURE OF THE INVENTION

An object of the present invention is to provide novel naphthyridine derivatives that exhibit superior pharmacological properties to the above-mentioned derivatives previously developed by the inventor and that are more useful in the pharmaceutical field.

To achieve the above-mentioned object, the inventor conducted intensive research and found that the new derivatives represented by general formula (1) below can achieve the object and accomplished the present invention.

The invention provides a novel naphthyridine derivative represented by the following general formula (1):

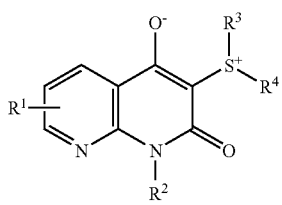

(1)

wherein $R^1$ represents a hydrogen atom or a lower alkyl group;

$R^2$ represents a hydrogen atom, a lower alkyl group, a cycloalkyl group, phenyl group, or a phenyl-lower alkyl group optionally having 1 to 3 lower alkoxy groups on the phenyl ring;

$R^3$ and $R^4$ each independently represent the group —Y—O—Z—$R^5$ (wherein Y is a lower alkylene group, Z is a single bond or a lower alkylene group, and $R^5$ is phenyl group optionally having 1 to 3 substituents selected from the group consisting of halogen atoms, lower alkoxy groups, lower alkyl groups, halogen-substituted lower alkyl groups, methylenedioxy group, hydroxyl group, 2,2-di(lower alkoxycarbonyl)ethyl groups and 2,2-di(lower alkoxycarbonyl)vinyl groups; or one of $R^3$ and $R^4$ is the group —Y—O—Z—$R^5$ (wherein Y, Z and $R^5$ are as defined above) and the other is a lower alkyl group, phenyl group, or a phenyl-lower alkyl group;

with the proviso that the case where $R^2$ is a phenyl-lower alkyl group optionally having 1 to 3 lower alkoxy groups on the phenyl ring and at least one of $R^3$ and $R^4$ is a benzyloxy-lower alkyl group having 1 to 3 lower alkoxy groups on the benzene ring is excluded.

The invention further provides a pharmaceutical composition that comprises the above naphthyridine derivative and a pharmaceutically acceptable carrier; in particular, a pharmaceutical composition that serves as an analgesic, a pharmaceutical composition that serves as a diabetic neuropathy treatment agent, and/or a pharmaceutical composition that serves as an adenosine enhancement agent.

Furthermore, the present invention provides a method for relieving pain in a patient, a method for treating diabetic neuropathy in a patient, or a method for enhancing adenosine in a patient, which comprises administrating an effective amount of the above-mentioned naphthyridine derivative to the patient in need of such treatment.

Hereafter, the derivative of the present invention is described in detail.

Specific examples of groups in the above-mentioned general formula (1) and other general formulae in the specification are mentioned below. In the specification, the word "lower" that is used to describe carbon-containing groups means "having 1 to 6 carbon atoms".

Examples of lower alkyl groups include methyl, ethyl, propyl, isopropyl, butyl, isobutyl, tert-butyl, pentyl, hexyl and like straight- or branched-chain alkyl groups having 1 to 6 carbon atoms.

Examples of cycloalkyl groups include cyclopropyl, cyclobutyl, cyclopentyl, cyclohexyl, cycloheptyl, cyclooctyl and like cycloalkyl groups having 3 to 8 carbon atoms.

Examples of lower alkoxy groups include methoxy, ethoxy, propoxy, isopropoxy, butoxy, pentyloxy, hexyloxy and like straight- or branched-chain alkoxy groups having 1 to 6 carbon atoms.

Examples of lower alkylene groups include methylene, ethylene, ethylidene, trimethylene, tetramethylene, pentamethylene, hexamethylene and like straight- or branched-chain alkylene groups having 1 to 6 carbon atoms.

Examples of halogen atoms include fluorine, chlorine, bromine, and iodine.

Examples of halogen-substituted lower alkyl groups include perhalogeno-($C_{1-6}$-alkyl) groups having halogen atoms selected from the group consisting of fluorine, chlorine, bromine and iodine, as substituents, and in particular, perfluoro-($C_{1-6}$-alkyl) groups. Specific examples thereof are trifluoromethyl, pentafluoroethyl, heptafluoropropyl, nonafluorobutyl, undecafluoropentyl, tridecafluorohexyl groups, etc.

Examples of 2,2-di(lower alkoxy-carbonyl)ethyl groups include 2,2-dimethoxycarbonylethyl, 2,2-diethoxycarbonylethyl, 2,2-dipropoxycarbonylethyl, 2,2-dibutoxycarbonylethyl, 2,2-dipentyloxycarbonylethyl, 2,2-dihexyloxycarbonylethyl and like 2,2-di($C_{1-6}$-alkoxy-carbonyl)ethyl groups.

Examples of 2,2-di(lower alkoxy-carbonyl)vinyl groups include 2,2-dimethoxycarbonylvinyl, 2,2-diethoxycarbonylvinyl, 2,2-dipropoxycarbonylvinyl, 2,2-dibutoxycarbonylvinyl, 2,2-dipentyloxycarbonylvinyl, 2,2-dihexyloxycarbonylvinyl and like 2,2-di($C_{1-6}$-alkoxy-carbonyl)vinyl groups.

Examples of phenyl-lower alkyl groups include benzyl, 1-phenylethyl, 2-phenylethyl, 3-phenylpropyl, 4-phenylbutyl, 5-phenylpentyl, 6-phenylhexyl and like phenyl-$C_{1-6}$-alkyl groups.

Examples of phenyl-lower alkyl groups optionally having 1 to 3 lower alkoxy groups on the phenyl ring include, in addition to the above-mentioned phenyl-lower alkyl groups, 2-methoxybenzyl, 3-methoxybenzyl, 4-methoxybenzyl, 4-ethoxybenzyl, 4-propoxybenzyl, 4-butoxybenzyl, 4-pentyloxybenzyl, 4-hexyloxybenzyl, 2,3-dimethoxybenzyl, 2,4-dimethoxybenzyl, 2,5-dimethoxybenzyl, 2,6-dimethoxybenzyl, 3,4-dimethoxybenzyl, 3,5-dimethoxybenzyl, 2,3,4-trimethoxybenzyl, 2,3,5-trimethoxybenzyl, 2,4,5-trimethoxybenzyl, 3,4,5-trimethoxybenzyl, 3,4,5-triethoxybenzyl, 1-(4-methoxyphenyl)ethyl, 2-(4-methoxyphenyl)ethyl, 3-(4-methoxyphenyl)propyl, 4-(4-methoxyphenyl)butyl, 5-(4-methoxyphenyl)pentyl, 6-(4-methoxyphenyl)hexyl, 1-(3,4,5-trimethoxyphenyl)ethyl, 2-(3,4,5-trimethoxyphenyl)ethyl, 3-(3,4,5-trimethoxyphenyl)propyl, 4-(3,4,5-trimethoxyphenyl)butyl, 5-(3,4,5-trimethoxyphenyl)pentyl, 6-(3,4,5-trimethoxyphenyl)hexyl and like phenyl-$C_{1-6}$-alkyl groups optionally having 1 to 3 $C_{1-6}$-alkoxy groups on the phenyl ring.

Examples of phenyl groups optionally having 1 to 3 substituents selected from the group consisting of halogen atoms, lower alkoxy groups, lower alkyl groups, halogen-substituted lower alkyl groups, methylenedioxy group, hydroxyl group, 2,2-di(lower alkoxy-carbonyl)ethyl groups and 2,2-di(lower alkoxy-carbonyl)vinyl groups are, in addition to unsubstituted phenyl group, the following:

2-chlorophenyl, 3-chlorophenyl, 4-chlorophenyl, 4-fluorophenyl, 4-bromophenyl, 4-iodophenyl, 2-methoxyphenyl, 3-methoxyphenyl, 4-methoxyphenyl, 4-ethoxyphenyl, 4-propoxyphenyl, 4-butoxyphenyl, 4-pentyloxyphenyl, 4-hexyloxyphenyl, 2-trifluoromethylphenyl, 3-trifluoromethylphenyl, 4-trifluoromethylphenyl, 4-pentafluoroethylphenyl, 4-heptafluoropropylphenyl, 4-nonafluorobutylphenyl, 4-undecafluoropentylphenyl, 4-tridecafluorohexylphenyl, 2,3-methylenedioxyphenyl, 3,4-methylenedioxyphenyl, 2-hydroxyphenyl, 3-hydroxyphenyl, 4-hydroxyphenyl, 2-(2,2-dimethoxycarbonylethyl)phenyl, 3-(2,2-dimethoxycarbonylethyl)phenyl, 4-(2,2-dimethoxycarbonylethyl)phenyl, 4-(2,2-diethoxycarbonylethyl)phenyl, 4-(2,2-dipropoxycarbonylethyl)phenyl, 4-(2,2-dibutoxycarbonylethyl)phenyl, 4-(2,2-dipentyloxycarbonylethyl)phenyl, 4-(2,2-dihexyloxycarbonylethyl)phenyl, 2-(2,2-dimethoxycarbonylvinyl)phenyl, 3-(2,2-dimethoxycarbonylvinyl)phenyl, 4-(2,2-dimethoxycarbonylvinyl)phenyl, 4-(2,2-diethoxycarbonylvinyl)phenyl, 4-(2,2-dipropoxycarbonylvinyl)phenyl, 4-(2,2-dibutoxycarbonylvinyl)phenyl, 4-(2,2-dipentyloxycarbonylvinyl)phenyl, 4-(2,2-dihexyloxycarbonylvinyl)phenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2,4,6-trichlorophenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 2,4,6-trimethoxyphenyl, 2,3,4-trimethoxyphenyl, 2,3,5-trimethoxyphenyl, 2,4,5-trimethoxyphenyl, 3,4,5-trimethoxyphenyl, 2,3-dimethylphenyl, 2,4-dimethylphenyl; 2,5-dimethylphenyl, 2,6-dimethylphenyl, 3,4-dimethylphenyl, 3,5-dimethylphenyl, 2,4,6-trimethylphenyl, 2,3,4-trimethylphenyl, 2,3,5-trimethylphenyl, 2,4,5-trimethylphenyl, 3,4,5-trimethylphenyl, 2,3-bis(trifluoromethyl)phenyl, 2,4-bis(trifluoromethyl)phenyl, 2,5-bis(trifluoromethyl)phenyl, 2,6-bis(trifluoromethyl)phenyl, 3,4-bis(trifluoromethyl)phenyl; 3,5-bis(trifluoromethyl)phenyl, 2,4,6-tris(trifluoromethyl)phenyl, 2,3,4-tris(trifluoromethyl)phenyl; 2,3,5-tris(trifluoromethyl)phenyl; 2,4,5-tris(trifluoromethyl)phenyl; 3,4,5-tris(trifluoromethyl)phenyl; 2,3-dihydroxyphenyl; 2,4-dihydroxyphenyl; 2,5-dihydroxyphenyl; 2,6-dihydroxyphenyl; 3,4-dihydroxyphenyl; 3,5-dihydroxyphenyl; 2,4,6-trihydroxyphenyl; 2,3,4-trihydroxyphenyl; 2,3,5-trihydroxyphenyl; 2,4,5-trihydroxyphenyl; 3,4,5-trihydroxyphenyl; 2,4-bis(2,2-dipentyloxycarbonylethyl)phenyl; 3,5-bis(2,2-dipentyloxy carbonylethyl)phenyl; 2,5-bis(2,2-dipentyloxy carbonylethyl)phenyl; 2,6-bis(2,2-dipentyloxy carbonylethyl)phenyl; 2,4,6-tris(2,2-dipentyloxy carbonylethyl)phenyl; 2,4-bis(2,2-dipentyloxy carbonylvinyl)phenyl; 3,5-bis(2,2-dipentyloxy carbonylvinyl)phenyl; 2,5-bis(2,2-dipentyloxy carbonylvinyl)phenyl; 2,6-bis(2,2-dipentyloxy carbonylvinyl)phenyl; 2,4,6-tris(2,2-dipentyloxy carbonylvinyl)phenyl; 3,4-methylenedioxy-5-methoxyphenyl; 2,3-methylenedioxy-4-methoxyphenyl; 2,3-methylenedioxy-5-methoxyphenyl; 5-hydroxy-3,4-methylenedioxyphenyl; 5-hydroxy-2,3-methylenedioxyphenyl; 4-hydroxy-2,3-methylenedioxyphenyl; 3-hydroxy-4,5-dimethoxyphenyl; 4-hydroxy-3,5-dimethoxyphenyl; 4-hydroxy-2,6-dimethoxyphenyl; 3,5-dihydroxy-4-methoxyphenyl; 2,6-dihydroxy-4-methoxyphenyl; 4-hydroxy-3,5-dimethylphenyl; 4-methoxy-3,5-dimethylphenyl; 4-hydroxy-3,5-di-t-butylphenyl; 4-methoxy-3,5-di-t-butylphenyl; 2-chloro-4-methoxyphenyl; 4-chloro-2-methoxyphenyl; 2-chloro-4-methylphenyl; 4-chloro-2-methylphenyl; 2-chloro-4-trifluoromethylphenyl; 4-chloro-2-trifluoromethylphenyl; 2-chloro-4,5-methylenedioxyphenyl; 5-chloro-2,3-methylenedioxyphenyl; 2-chloro-4-hydroxyphenyl; 4-chloro-2-hydroxyphenyl; 2-chloro-4-(2,2-dimethoxycarbonylethyl)phenyl; 4-chloro-2-(2,2-dimethoxycarbonylethyl)phenyl; 2-chloro-4-(2,2-dimethoxycarbonylvinyl)phenyl; 4-chloro-2-(2,2-dimethoxycarbonylvinyl)phenyl; 3-methoxy-4-methylphenyl; 4-methoxy-3-methylphenyl; 3-methoxy-4-trifluoromethylphenyl; 4-methoxy-3-trifluoromethylphenyl; 3-hydroxy-4-methoxyphenyl; 4-hydroxy-3-methoxyphenyl; 4-(2,2-dimethoxycarbonylethyl)-2-methoxyphenyl; 2-(2,2-dimethoxycarbonylethyl)-4-methoxyphenyl; 4-(2,2-dimethoxycarbonylvinyl)-2-methoxyphenyl; 2-(2,2-dimethoxycarbonylvinyl)-4-methoxyphenyl; 3-methyl-4-trifluoromethylphenyl; 4-methyl-3-trifluoromethylphenyl; 4-methyl-2,3-methylenedioxyphenyl; 2-methyl-3,4-methylenedioxyphenyl; 3-hydroxy-4-methylphenyl; 4-hydroxy-3-methylphenyl; 4-(2,2-dimethoxycarbonylethyl)-2-methylphenyl; 2-(2,2-dimethoxycarbonylethyl)-4-methylphenyl; 4-(2,2-dimethoxycarbonylvinyl)-2-methylphenyl; 2-(2,2-dimethoxycarbonylvinyl)-4-methylphenyl; 2,3-methylenedioxy-4-trifluoromethylphenyl; 3,4-methylenedioxy-5-trifluoromethylphenyl; 3-hydroxy-4-trifluoromethylphenyl; 4-hydroxy-3-trifluoromethylphenyl, 4-(2,2-dimethoxycarbonylethyl)-2-trifluoromethylpheny, 2-(2,2-dimethoxycarbonylethyl)-4-trifluoromethylphenyl, 4-(2,2-dimethoxycarbonylvinyl)-2-trifluoromethylphenyl, 2-(2,2-dimethoxycarbonylvinyl)-4-trifluoromethylphenyl, 2,3-methylenedioxy-5-(2,2-dimethoxycarbonylethyl)phenyl, 2,3-methylenedioxy-5-(2,2-dimethoxycarbonylvinyl)phenyl, 4-(2,2-dimethoxycarbonylethyl)-2-hydroxyphenyl, 2-(2,2-dimethoxycarbonylethyl)-4-hydroxyphenyl, 4-(2,2-dimethoxycarbonylvinyl)-2-hydroxyphenyl, 2-(2,2-dimethoxycarbonylvinyl)-4-hydroxyphenyl, 4-(2,2-dimethoxycarbonylethyl)-2-(2,2-dimethoxycarbonylvinyl)

phenyl, 2-(2,2-dimethoxycarbonylethyl)-4-(2,2-dimethoxycarbonylvinyl)phenyl group, etc.

Among the naphthyridine derivatives of the invention, the group comprising the compounds defined in (1)–(6) below is preferable. Hereinafter, this group may be referred to as group A compounds of the invention.

(1) A naphthyridine derivative represented by the formula (1) wherein one of $R^3$ and $R^4$ is a lower alkyl group.

(2) A naphthyridine derivative according to (1), wherein $R^1$ is a hydrogen atom.

(3) A naphthyridine derivative according to (2), wherein $R^2$ is a phenyl-lower alkyl group optionally having 1 to 3 lower alkoxy groups on the phenyl ring.

(4) A naphthyridine derivative according to (3), wherein Z is a single bond.

(5) A naphthyridine derivative according to (4), wherein $R^5$ is phenyl having 1 to 3 lower alkoxy groups as substituents.

(6) A naphthyridine derivative according to (5), wherein $R^2$ is benzyl optionally having 1 to 3 lower alkoxy groups on the phenyl ring.

Among the above-described group A compounds of the invention, compounds of (4)–(6) exhibit especially excellent pharmacological activity.

Among the naphthyridine derivatives of the present invention, another preferable group include the compounds defined in (7)–(9) mentioned below. Hereafter, this group may be called group B compounds of the invention.

(7) A naphthyridine derivative represented by the formula (1), wherein one of $R^3$ and $R^4$ is a lower alkyl group and Z is a single bond.

(8) A naphthyridine derivative according to (7), wherein $R^5$ is phenyl having three lower alkoxy groups as substituents.

(9) A naphthyridine derivative according to (7), wherein $R^5$ is 3,4,5-tri-lower alkoxy-phenyl group.

Each compound belonging to group B compounds of the invention exhibits excellent pharmacological activity with minimal side effects. Among these, the compounds defined in (8) and (9) have more potent pharmacological activity.

The specific compounds encompassed in the preferable naphthyridine derivatives of the present invention in terms of favorable pharmacological activity and side effects are listed in (10) below:

(10) 1-(3,4,5-trimethoxybenzyl)-3-[methyl-2-(3,4,5-trimethoxyphenoxy)ethylsulfonium]-1,8-naphthyridine-2(1H)-one-4-olate, 1-benzyl-3-[ethyl-3-(3,4,5-trimethoxyphenoxy)propylsulfonium]-1,8-naphthyridine-2(1H)-one-4-olate, 1-methyl-3-[methyl-2-(3,4,5-trimethoxyphenoxy)ethylsulfonium]-1,8-naphthyridine-2(1H)-one-4-olate, 1-benzyl-3-[methyl-3-(3,4,5-trimethoxyphenoxy)propylsulfonium]-1,8-naphthyridine-2(1H)-one-4-olate, and 1-(4-methoxybenzyl)-3-[methyl-3-(3,4,5-trimethoxyphenoxy)propylsulfonium]-1,8-naphthyridine-2(1H)-one-4-olate.

Among these, 1-benzyl-3-[methyl-3-(3,4,5-trimethoxyphenoxy)propylsulfonium]-1,8-naphthyridine-2(1H)-one-4-olate is the most preferable.

The naphthyridine derivatives of the invention can be produced by various processes. Exemplary processes are shown below with reference to reaction schemes.

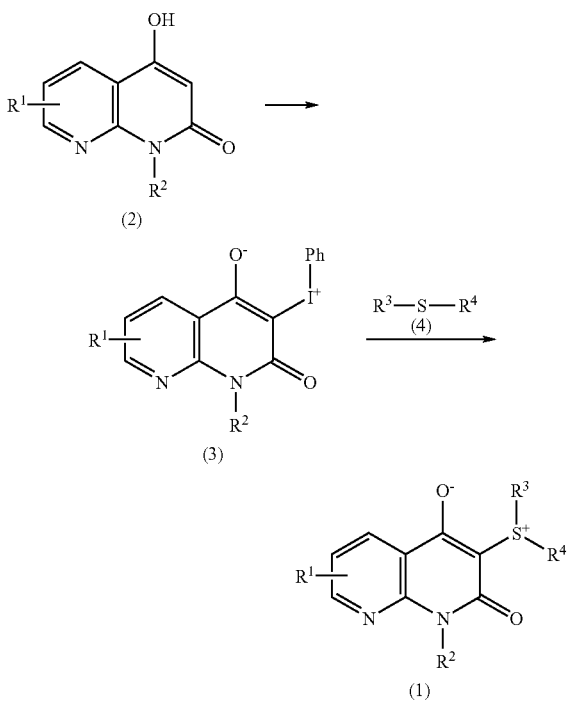

[Reaction Scheme-1]

[wherein $R^1$, $R^2$, $R^3$ and $R^4$ are as defined above, and Ph represents phenyl.]

In Reaction Scheme-1, compound (2) is reacted with iodobenzene diacetate in the presence of an alkali, giving compound (3). Water is suitably used as a solvent in the reaction. Useful alkalis include, for example, sodium carbonate, potassium carbonate, sodium hydrogen carbonate and potassium hydrogen carbonate. The alkali and iodobenzene diacetate are each preferably used in an equimolar amount to slight excess relative to the starting compound. The reaction is carried out at a temperature from about 0° C. to about room temperature and is completed in about 1 to 10 hours.

Subsequently, the resulting compound (3) is reacted with thioether derivative (4), giving compound (1) of the invention. The reaction may be carried out using a lower alcohol, such as methanol, ethanol, trifluoroethanol or the like as a solvent and adding a suitable amount of an acid catalyst, such as p-toluenesulfonic acid, acetic acid or the like. Thioether derivative (4) is preferably used in an amount of about 1 to 10 moles per mole of compound (3). The acid catalyst is preferably used in an amount of 0.005 to 0.5 moles per mole of compound (3). The reaction is carried out at a temperature in the range from room temperature to reflux temperature and is completed in about 10 minutes to 24 hours.

In the above process, compound (2) used as a starting compound can be produced, for example, by following the steps below.

[Reaction Scheme-2]

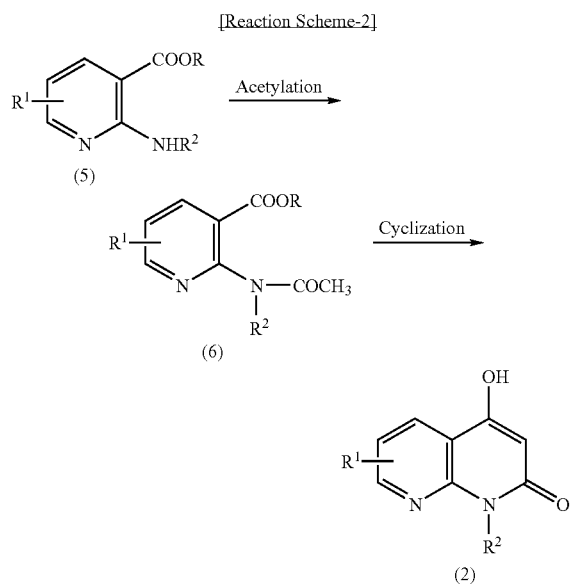

[wherein $R^1$ and $R^2$ are as defined above, and R represents a lower alkyl group.]

The acetylation reaction of compound (5) shown in Reaction Scheme-2 is conducted by heating compound (5) in an excess of acetic anhydride at 100° C. to a reflux temperature for 10 to 100 hours. Cyclization of acetamide derivative (6) obtained by this reaction is carried out by heating acetamide derivative (6) in an aromatic hydrocarbon inert solvent, such as toluene, xylene, mesitylene, cumene, and cymene, in the presence of a base such as potassium-t-butoxide or sodium ethoxide. The preferable amount of base is 1 to 5 times of moles per mole of starting compound. The heating temperature is in the range from about 100° C. to reflux temperature, and heating time is in the range from about 0.5 to 5 hours.

Compound (1) of the invention obtained by the above process is considered to have the resonance structures as shown below. Therefore, the compound of the present invention can be represented by any one of the following structural formulae.

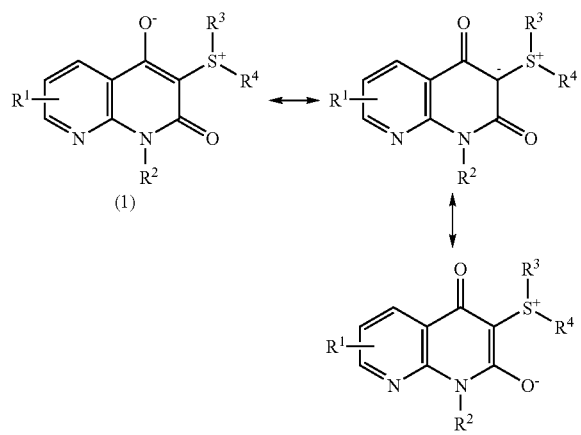

The compounds of the invention can be easily isolated and purified by conventional separation and purification methods. These methods include those generally employed, such as adsorption chromatography, preparative thin-layer chromatography, recrystallization and solvent extraction, etc.

Some of the compounds of the invention are optical isomers with sulfur and/or carbon as an asymmetric center. The present invention includes both racemates, which are a mixture of such optical isomers, and individual optically active forms, which are optical isomers. The optically active isomers can be isolated by conventional methods, such as methods using known optical resolving agents.

The compound represented by formula (1) of the invention has excellent analgesic effects and is useful as a medicine, particularly as an analgesic. In particular, the compound is effective in relieving postoperative pain and cancer pain. The compound of the invention is also useful as a diabetic neuropathy treatment agent or an adenosine enhancement agent. The compound of the present invention is characterized in that it exhibits minimal side effects, such as hypertrophy of the thyroid gland, than the naphthyridine derivative that has been previously developed by the inventor.

The present invention provides a pharmaceutical composition comprising the compound of the invention represented by the above-mentioned general formula (1) as an active ingredient. This pharmaceutical composition is formed into general pharmaceutical preparations using the compound of the invention and pharmaceutically acceptable carriers and then administered.

Examples of pharmaceutically acceptable carriers for use in the pharmaceutical compositions of the invention are conventional diluents or excipients, such as fillers, extenders, binders, humectants, disintegrators, surfactants, lubricants and the like, which are suitably selected and used according to the desired unit dosage form.

A suitable unit dosage form can be selected from a variety of forms according to the therapeutic purpose. Typical examples are tablets, pills, powders, solutions, suspensions, emulsions, granules, capsules, suppositories, injections (solutions, suspensions, etc.), ointments and the like.

In producing tablets, usable as the above pharmaceutically acceptable carriers are excipients, such as lactose, sucrose, sodium chloride, glucose, urea, starch, calcium carbonate, kaolin, crystalline cellulose, silicic acid and potassium phosphate; binders such as water, ethanol, propanol, simple syrup, glucose syrup, starch solution, gelatin solution, carboxymethyl cellulose, hydroxypropyl cellulose, methyl cellulose and polyvinyl pyrrolidone; disintegrators such as sodium carboxymethyl cellulose, calcium carboxymethyl cellulose, low-substituted hydroxypropyl cellulose, dry starch, sodium alginate, agar powder, laminaran powder, sodium hydrogen-carbonate and calcium carbonate; surfactants such as polyoxyethylene sorbitan fatty acid esters, sodium lauryl sulfate and stearic acid monoglyceride; disintegration inhibitors such as sucrose, stearin, cacao butter and hydrogenated oil; absorption promoters such as quaternary ammonium bases and sodium lauryl sulfate; humectants such as glycerin and starch; adsorbents such as starch, lactose, kaolin, bentonite and colloidal silicic acid; and lubricants such as purified talc, salts of stearic acid, boric acid powder and polyethylene glycol. If necessary, the tablets can be made into coated tablets, such as sugar-coated tablets, gelatin-coated tablets, enteric tablets, film-coated tablets, double-layered tablets or multiple-layered tablets.

In producing pills, usable as pharmaceutically acceptable carriers are excipients such as glucose, lactose, starch, cacao butter, hydrogenated vegetable oil, kaolin and talc; binders such as gum arabic powder, tragacanth powder, gelatin and ethanol; and disintegrators such as laminaran and agar.

In producing suppositories, usable as pharmaceutically acceptable carriers are polyethylene glycol, cacao butter, higher alcohols or their esters, gelatin, semisynthetic glycerides and the like.

Capsules are usually manufactured in a conventional manner by blending the compound of the invention with one or more pharmaceutically acceptable carriers as exemplified above and encapsulating the mixture into hard gelatin capsule shells, soft gelatin capsule shells, etc.

When the compound of the invention is to be provided in an injectable form such as a solution, an emulsion or a suspension, the preparation is preferably sterilized and rendered isotonic to the blood. Diluents for use in such preparation include, for example, water, ethanol, macrogols, propylene glycol, ethoxylated isostearyl alcohol, polyoxyisostearyl alcohol, polyoxyethylene sorbitan fatty acid esters and the like. In this case, sodium chloride, glucose or glycerin may be added to the pharmaceutical composition in an amount sufficient to provide an isotonic solution. General solubilizers, buffers, soothing agents, etc., may also be added thereto.

In preparing ointments in the form of pastes, creams, gels, etc., usable as diluents are white petrolatum, paraffin, glycerin, cellulose derivatives, polyethylene glycol, silicone, bentonite and the like.

Furthermore, if desired, coloring agents, preservatives, aromatics, flavors, sweeteners or other medicines may be incorporated into the pharmaceutical composition of the invention.

The proportion of the compound of the invention (active ingredient compound) in the pharmaceutical composition is not critical and can be selected from a broad range. It is generally preferable that the compound account for about 0.5 to about 90 wt. %, preferably about 1 to about 85 wt. % of the pharmaceutical composition.

There is no limitation to the methods for administering the pharmaceutical compositions of the invention. Thus, an appropriate method can be selected according to the dosage form, patient's age, sex and other conditions, severity of disease, etc. For example, tablets, pills, solutions, suspensions, emulsions, granules and capsules are orally administered. Injections are administered alone or in admixture with glucose, amino acid or like conventional infusions by the intravenous route or by the intramuscular, intradermal, subcutaneous or intraperitoneal route, while suppositories are intrarectally administered.

The dosage of the pharmaceutical preparation of the invention is suitably selected according to the intended use, patient's age, sex and other conditions, severity of disease, etc., but may be such that the dosage of the compound of the invention as the active ingredient is preferably about 0.5–20 mg, preferably about 1–10 mg, per kg body weight a day, for human adult. The pharmaceutical preparation may be administered once a day or in 2–4 divided doses a day.

BEST MODE FOR CARRYING OUT THE INVENTION

Hereunder, to illustrate the present invention in more detail, examples of manufacturing methods of the starting compounds used in producing the compounds of the present invention are described and then manufacturing methods of the compounds of the present invention are described as Examples.

In each Example, unless otherwise stated, $^1$H-NMR spectra were measured in dimethyl sulfoxide-$d_6$ (DMSO-$d_6$) solvent using tetramethylsilane (TMS) as an internal standard.

Reference Example 1

(1) Manufacture of 1-benzyl-4-hydroxy-1,8-naphthyridine-2(1H)-one

In 400 ml of acetic anhydride was dissolved 36.7 g of methyl 2-benzylaminonicotinate, followed by stirring at 160° C. for 48 hours. After completion of the reaction, acetic anhydride was removed under reduced pressure, the residue was dissolved in 400 ml of diethyl ether, washed twice with saturated sodium bicarbonate solution and once with water, dried over anhydrous magnesium sulfate and concentrated under reduced pressure to give 39.0 g of oily methyl 2-(N-acetyl-N-benzyl)aminonicotinate.

Then, 22.5 g of the compound obtained above was dissolved in 300 ml of xylene, 21.3 g of potassium-t-butoxide was added thereto at room temperature, and the mixture was stirred at 150° C. for 2 hours. After cooling, the mixture was extracted with 250 ml of water and aqueous citric acid solution was added to the aqueous layer to adjust the pH of the aqueous layer to 3. The precipitated crystals were filtered and washed with methanol, giving 20.5 g of crystalline 1-benzyl-4-hydroxy-1,8-naphthyridine-2(1H)-one.

Melting point: 250–253° C. $^1$H-NMR($\delta$: ppm): 5.55(2H, s), 5.97(1H, s), 7.15–7.35(6H, m), 8.26(1H, d, J=7.7), 8.60 (1H, d, J=4.7), 11.79(1H, brs)

(2)–(8) Manufacture of the Following Compounds

Following the procedure described in (1), and using appropriate starting materials, compounds described in (2)–(8) below were synthesized.

(2) 4-hydroxy-1,8-naphthyridine-2(1H)-one

Melting point: over 300° C. $^1$H-NMR($\delta$: ppm): 5.76(1H, s), 7.21(1H, dd, J=4.7, 7.7), 8.14(1H, d, J=7.7), 8.51(1H, d, J=4.7), 11.58(2H, brs)

(3) 1-(4-methoxybenzyl)-4-hydroxy-1,8-naphthyridine-2(1H)-one

Melting point: 256–259° C. $^1$H-NMR($\delta$: ppm): 3.69(3H, s), 5.48(2H, s), 5.96 (1H, s), 6.81(2H, d, J=8.7), 7.23(2H, d, J=8.7), 7.28(1H, dd, J=4.7, 7.7), 8.25(1H, d, J=7.7), 8.62 (1H, d, J=4.7), 11.76(1H, brs)

(4) 1-(3,4,5-trimethoxybenzyl)-4-hydroxy-1,8-naphthyridine-2(1H)-one

Melting point: 254–257° C. $^1$H-NMR($\delta$: ppm): 3.60(3H, s), 3.67(6H, s), 5.47(2H, s), 5.96(1H, s), 6.60(2H, s), 7.30 (1H, dd, J=4.7, 7.7), 8.26(1H, d, J=7.7), 8.64(1H, d, J=4.7), 11.80(1H, brs)

(5) 1-benzyl-4-hydroxy-7-methyl-1,8-naphthyridine-2(1H)-one

Melting point: 261–264° C. $^1$H-NMR($\delta$:ppm): 2.49(3H, s), 5.49(2H, s), 5.87(1H, s), 7.10(1H, d, J=7.9), 7.12–7.29 (5H, m), 8.09(1H, d, J=7.9), 11.78(1H, brs)

(6) 4-hydroxy-1-n-propyl-1,8-naphthyridine-2(1H)-one

Melting point: 257–259° C. $^1$H-NMR($\delta$: ppm): 0.89(3H, t, J=7.4), 1.51–1.68(2H, m), 4.26(2H, t, J=7.4), 5.89(1H, s), 7.28(1H, dd, J=4.5, 7.6), 8.23(1H, d, J=7.6), 8.64(1H, d, J=4.5), 11.70(1H, brs)

(7) 1-cyclohexyl-4-hydroxy-1,8-naphthyridine-2(1H)-one

Melting point: 265–268° C. $^1$H-NMR($\delta$: ppm): 1.11–1.91 (8H, m), 2.58–2.88(2H, m), 5.30–5.67(1H, m), 5.85(1H, s), 7.26(1H, dd, J=4.7, 7.7), 8.21(1H, d, J=7.7), 8.63(1H, d, J=4.7), 11.57(1H, brs)

(8) 4-hydroxy-1-phenyl-1,8-naphthyridine-2(1H)-one

Melting point: 288–290° C. $^1$H-NMR($\delta$:ppm): 5.94(1H, s), 7.17–7.30(3H, m), 7.35–7.52(3H, m), 8.26(1H, d, J=7.9), 8.39(1H, d, J=4.7), 11.51(1H, brs)

(9) Manufacture of 1-benzyl-3-phenyliodonium-1,8-naphthyridine-2(1H)-one-4-olate Sodium carbonate (3.1 g) (29 mmol) was dissolved in 200 ml of water in which 7.0 g (28 mmol) of compound (1) was then dissolved. Further, 9.0 g (28 mmol) of iodobenzene diacetate was added thereto at room temperature, followed by stirring for 5 hours. After completion of the reaction, the crystals precipitated were collected by filtration, washed sequentially with water, methanol and ether, and dried under reduced pressure at room temperature for 20 hours to give 10.1 g of the title compound.

Melting point: 147–149° C. (decomposition) $^1$H-NMR($\delta$: ppm): 5.56(2H, s), 7.11–7.26(6H, m), 7.33–7.54(3H, m), 7.84(2H,d, J=7.4), 8.32(1H, d, J=7.4), 8.50(1H, d, J=4.5)

(10)–(16) Manufacture of the Following Compounds

Following the procedure described in (9), and using appropriate starting materials, compounds (10)–(16) described below were synthesized.

(10) 3-phenyliodonium-1,8-naphthyridine-2(1H)-one-4-olate

Melting point: over 300° C. $^1$H-NMR($\delta$: ppm): 7.10(1H, dd, J=4.7, 7,7), 7.35–7.53(3H, m), 7.81(2H, d, J=7.4), 8.20 (1H, d, J=7.7), 8.42(1H, d, J=4.7), 11.01(1H, s)

(11) 1-(4-methoxybenzyl)-3-phenyliodonium-1,8-naphthyridine-2(1H)-one-4-olate

Melting point: 128–130° C. $^1$H-NMR($\delta$: ppm): 3.68(3H, s), 5.48(2H, s), 6.80(2H, d, J=8.9), 7.15(1H, dd, J=4.9, 7.9), 7.22(1H, d, J=8.9), 7.36–7.55(3H, m), 7.84(1H, d, J=7.4), 8.31(1H, d, J=7.9), 8.51(1H, d, J=4.9)

(12) 3-phenyliodonium-1-(3,4,5-trimethoxybenzyl)-1,8-naphthyridine-2(1H)-one-4-olate Melting point: 132–134° C. $^1$H-NMR($\delta$: ppm): 3.58(3H, s), 3.60(3H, s), 5.48(2H, s), 6.56(2H, s), 7.16(1H, dd, J=4.7, 7.7), 7.35–7.55(3H, m), 7.86(2H, d, J=7.7), 8.33(1H, d, J=7.7), 8.52(1H, d, J=4.7)

(13) 1-benzyl-7-methyl-3-phenyliodonium-1,8-naphthyridine-2(1H)-one-4-olate

Melting point: 139–140° C. $^1$H-NMR($\delta$: ppm): 2.47(3H, s), 5.53(2H, s), 7.01(1H, d, J=7.9), 7.10–7.53(8H, m), 7.83 (2H, d, J=8.4), 8.20(1H, d, J=7.9)

(14) 3-phenyliodonium-1-n-propyl-1,8-naphthyridine-2(1H)-one-4-olate

Melting point: 133–135° C. $^1$H-NMR($\delta$: ppm)[CDCl$_3$]: 0.91(3H, t, J=7.5), 1.45–1.61(2H, m), 4.20(2H, t, J=7.6), 7.04(1H, dd, J=4.6, 7.6), 7.32–7.50(3H, m), 7.94(2H, d, J=8.5), 8.38(1H, d, J=7.6), 8.47(1H, d, J=4.6)

(15) 1-cyclohexyl-3-phenyliodonium-1,8-naphthyridine-2(1H)-one-4-olate

Melting point: 136–138° C. $^1$H-NMR($\delta$: ppm): 1.13–1.87 (8H, m), 2.50–2.75(2H, m), 5.30–5.50(1H, m), 7.14(1H, dd, J=4.6, 7.7), 7.35–7.53(3H, m), 7.83(2H, d, J=8.2), 8.30(1H, d, J=7.7), 8.53(1H, d, J=4.6)

(16) 1-phenyl-3-phenyliodonium-1,8-naphthyridine-2(1H)-one-4-olate

Melting point: 141–143° C. $^1$H-NMR($\delta$: ppm)[CDCl$_3$]: 7.07(1H, dd, J=4.6, 7.6), 7.22(1H, d, J=7.3), 7.31–7.56(6H, m), 8.01(2H, d, J=7.6), 8.39(1H, d, J=4.6), 8.49(1H, d, J=7.6)

(17)–(20) Manufacture of the Following Compounds

Following the procedure described in (1), and using appropriate starting materials, compounds described in (17) and (18) below were synthesized. Compounds described in (19) and (20) below were synthesized following the procedure described in (9), and using appropriate starting materials.

(17) 1-ethyl-4-hydroxy-1,8-naphthyridine-2(1H)-one

(18) 4-hydroxy-1-methyl-1,8-naphthyridine-2(1H)-one

(19) 1-ethyl-3-phenyliodonium-1,8-naphthyridine-2(1H)-one-4-olate

(20) 1-methyl-3-phenyliodonium-1,8-naphthyridine-2(1H)-one-4-olate

EXAMPLE 1

Manufacture of 1-benzyl-3-[methyl-3-(3,4,5-trimethoxyphenoxy)propylsulfonium]-1,8-naphthyridine-2(1H)-one-4-olate The compound obtained in (9) (2.3 g, 5.1 mmol), 1.7 g (6.2 mmol) of methyl-3-(3,4,5-trimethoxyphenoxypropyl) sulfide and 30 mg of p-toluenesulfonic acid were dissolved in 20 ml of trifluoroethanol and stirred at room temperature for 30 minutes. After completion of the reaction, the trifluoroethanol was evaporated off and the residue was purified by silica gel column chromatography (developing solvent; methanol:chloroform=1:25). The crystals obtained were washed with methanol to provide 2.4 g of the title compound.

EXAMPLES 2–38

Compounds of the invention having the structures shown in Tables 1–5 below were prepared following the procedure of Example 1. Subsequent tables show the melting points and $^1$H-NMR analyses of the compounds.

TABLE 1

| Example 1 | Example 2 |
|---|---|
| Structral Formula: | Structral Formula: |
| 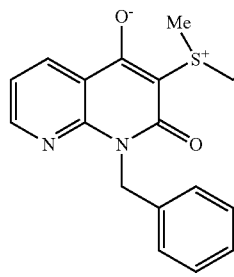 | 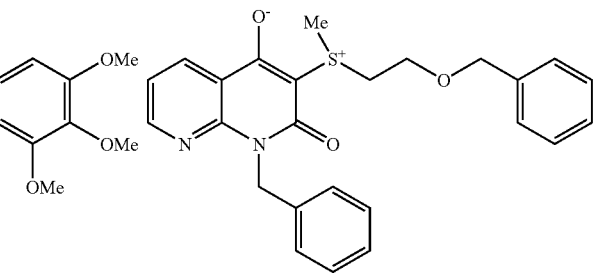 |

TABLE 1-continued
Example 3
Structral Formula:
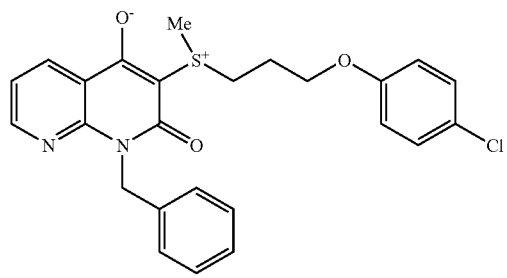
Example 4
Structral Formula:
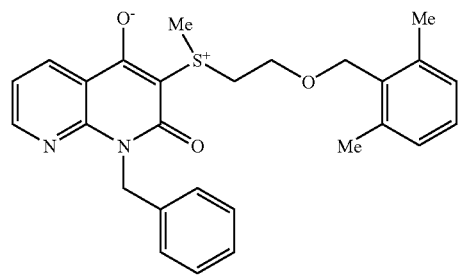
Example 5
Struactral Formula:
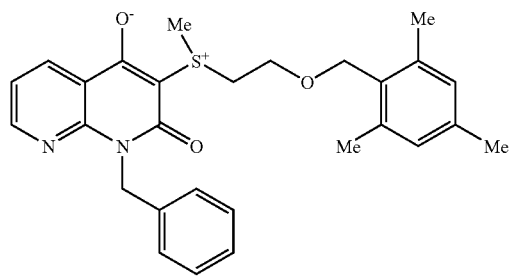
Example 6
Structral Formula:
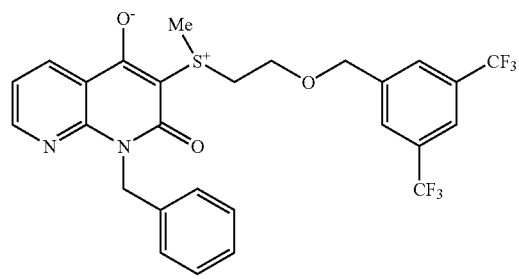
Example 7
Structral Formula:
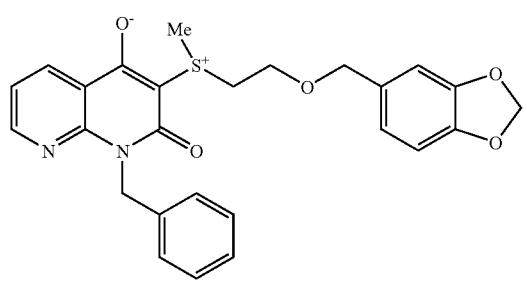
Example 8
Structral Formula:
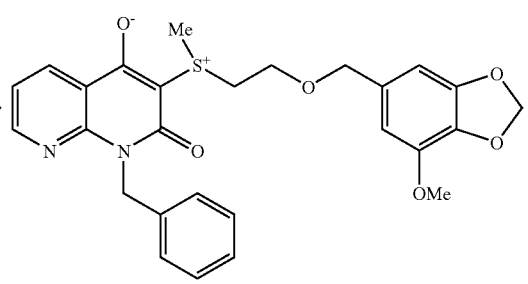
Example 9
Structral Formula:
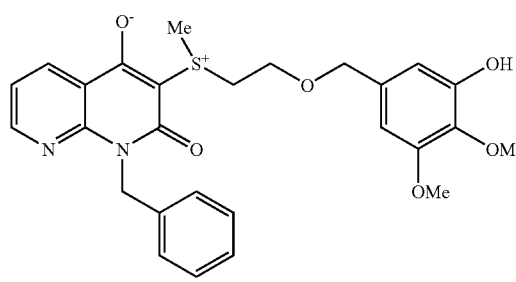
Example 10
Structral Formula:
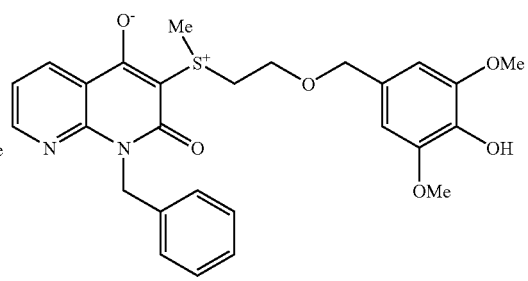

TABLE 2
Example 11
Structral Formula:
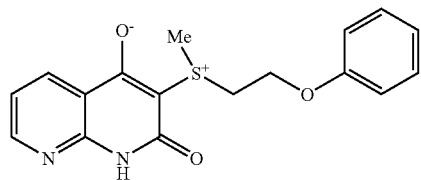
Example 12
Structral Formula:
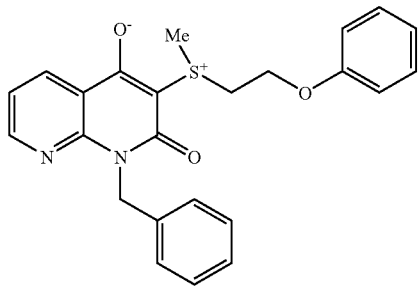
Example 13
Structral Formula:
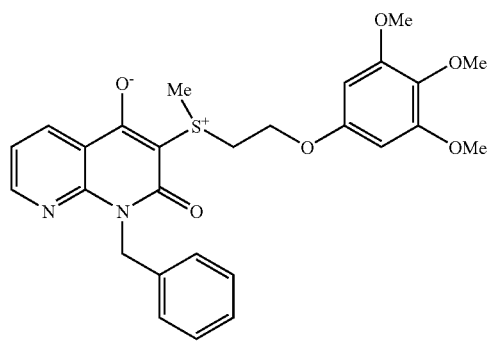
Example 14
Structral Formula:
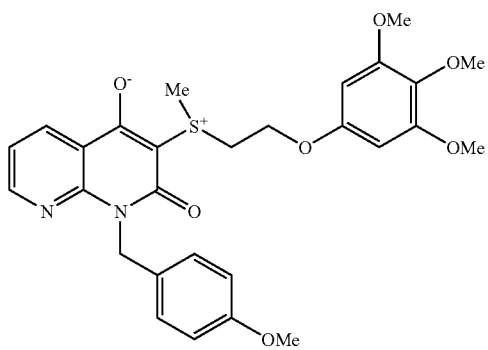
Example 15
Structral Formula:
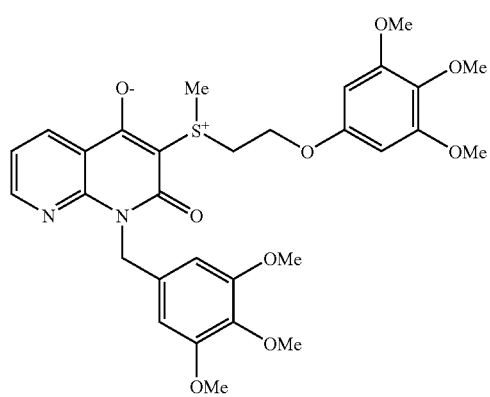
Example 16
Structral Formula:
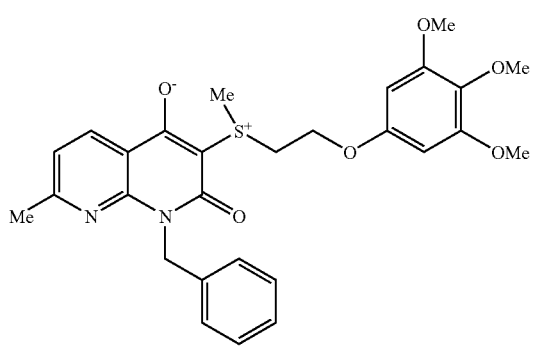
Example 17
Structral Formula:
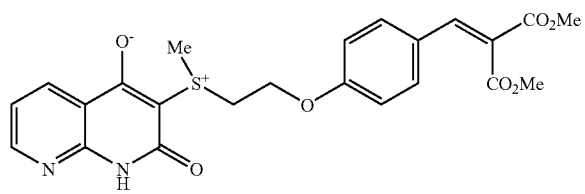
Example 18
Structral Formula:
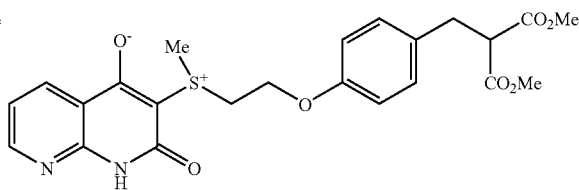

TABLE 2-continued
Example 19
Structral Formula:
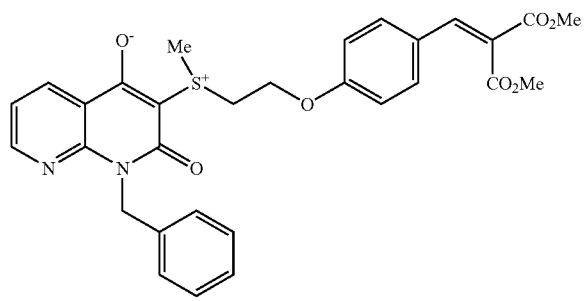
Example 20
Structral Formula:
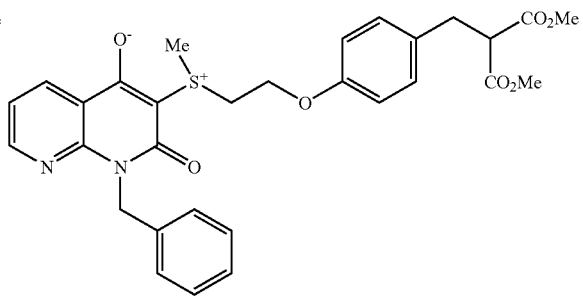
TABLE 3
Example 21
Structral Formula:
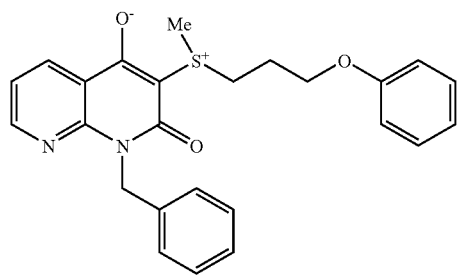
Example 22
Structral Formula:
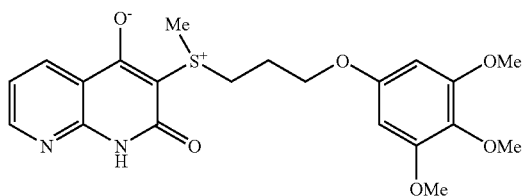
Example 23
Structral Formula:
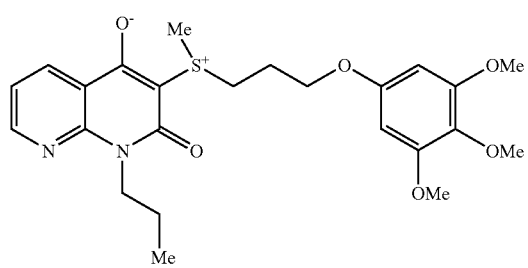
Example 24
Structral Formula:
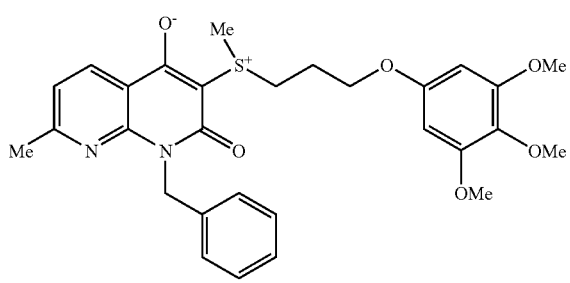
Example 25
Structral Formula:
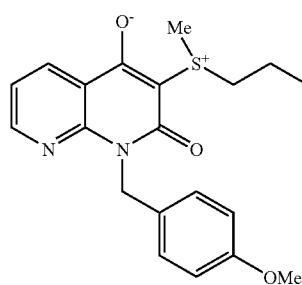
Example 26
Structral Formula:
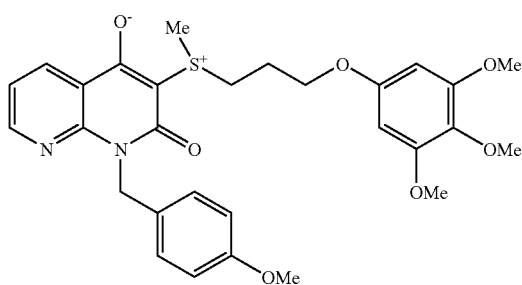

TABLE 3-continued
Example 27
Structral Formula:
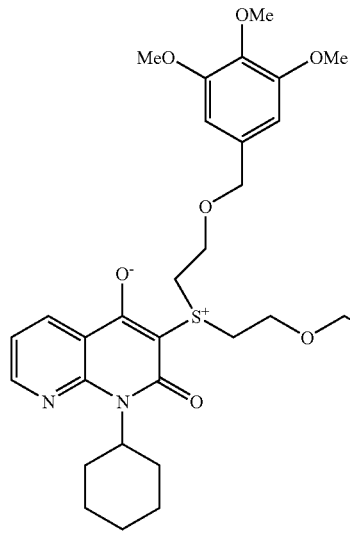
Example 28
Structral Formula:
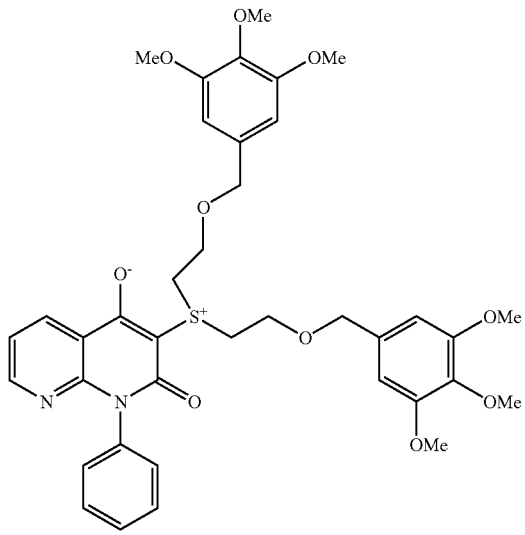
TABLE 4
Example 29
Structral Formula:
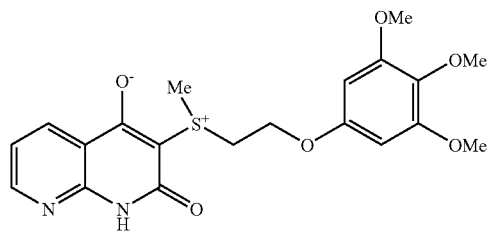
Example 30
Structral Formula:
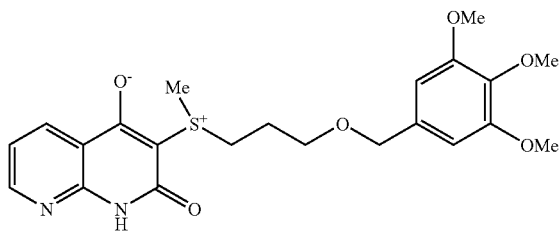
Example 31
Structral Formula:
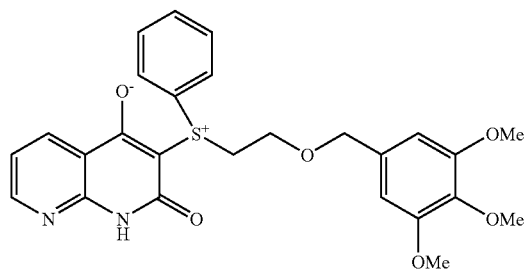
Example 32
Structral Formula:
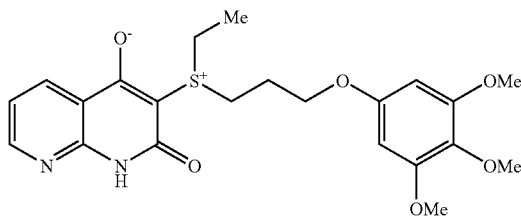

TABLE 4-continued
Example 33
Structral Formula:
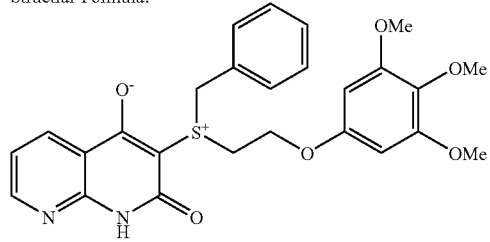
Example 34
Structral Formula:
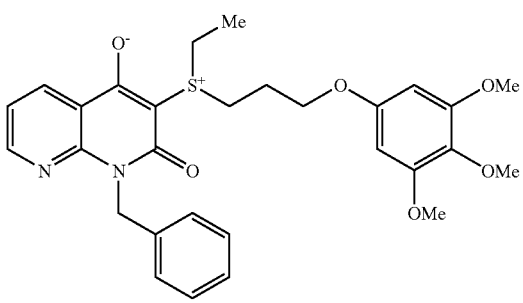
Example 35
Structral Formula:
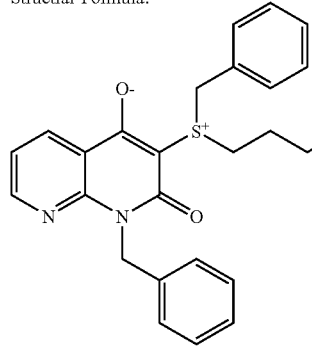
Example 36
Structral Formula:
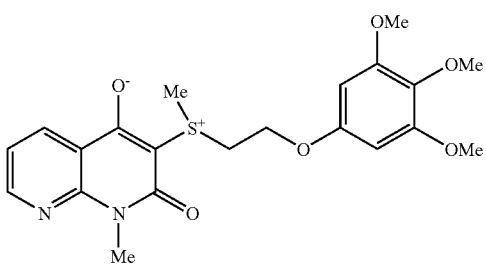
TABLE 5
Example 37
Structral Formula:
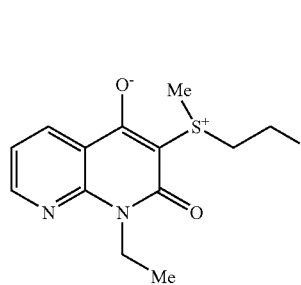
Example 38
Structral Formula:
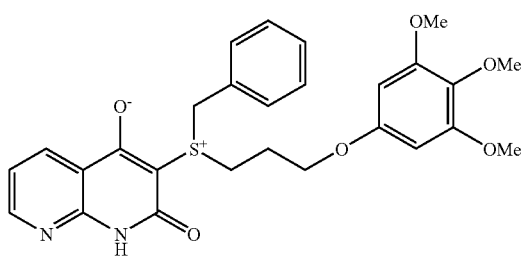
TABLE 6
| Example No. | Melting point (° C.) | Example No. | Melting point (° C.) | Example No. | Melting point (° C.) | Example No. | Melting point (° C.) |
| --- | --- | --- | --- | --- | --- | --- | --- |
| 1 | 147–149 | 2 | 130–132 | 21 | 101–103 | 22 | 126–128 |
| 3 | 145–147 | 4 | 161–163 | 23 | 84–86 | 24 | 123–124 |
| 5 | 165–167 | 6 | 157–159 | 25 | 136–138 | 26 | 100–102 |
| 7 | 124–126 | 8 | 84–87 | 27 | 89–91 | 28 | 156–157 |
| 9 | 132–134 | 10 | 121–123 | 29 | 220–222 | 30 | 161–163 |
| 11 | 158–160 | 12 | 120–122 | 31 | 203–205 | 32 | 120–122 |
| 13 | 100–102 | 14 | 165–167 | 33 | 182–184 | 34 | 96–98 |
| 15 | 135–137 | 16 | 114–116 | 35 | 110–113 | 36 | 186–188 |
| 17 | 203–205 | 18 | 183–186 | 37 | 157–159 | 38 | 164–166 |
| 19 | 151–153 | 20 | 123–124 | | | | |

TABLE 7

| Example No. | $^1$H-NMR (δ: ppm) |
|---|---|
| 1 | 1.95–2.10(2H, m), 3.18(3H, s), 3.43–3.55(1H, m), 3.56(3H, s), 3.70(6H, s), 4.02(2H, t, J=6.4), 4.07–4.20(1H, m), 5.45(2H, s), 6.19(2H, s), 7.16(1H, dd, J=4.5, 7.4), 7.19–7.25(5H, m), 8.28(1H, d, J=7.4), 8.48(1H, d, J=4.5) |
| 2 | 3.13(3H, s), 3.53–3.62(1H, m), 3.66–3.83(2H, m), 4.13–4.24(1H, m), 4.45(2H, s), 5.47(2H, s), 7.10–7.30(11H, m), 8.30(1H, d, J=7.6), 8.50(1H, d, J=4.6) |
| 3 | 3.12(3H, s), 3.50–3.59(1H, m), 3.65–3.82(2H, m), 4.13–4.26(1H, m), 4.43(2H, m), 5.46(2H, m), 7.14–7.30(10H, m), 8.29(1H, d, J=7.4), 8.50(1H, d, J=4.9) |
| 4 | 2.27(6H, s), 3.60(3H, s), 3.52–3.65(1H, m), 3.66–3.86(2H, m), 4.08–4.20(1H, m), 4.45(2H, s), 5.47(2H, s), 6.92–7.09(3H, m), 5.96(1H, s), 7.17(1H, dd, J=4.8, 7.6), 8.27(1H, d, J=7.6), 8.49(1H, d, J=4.8) |
| 5 | 2.16(3H, s), 2.22(3H, s), 3.08(3H, s), 3.46–3.61(1H, m), 3.64–3.83(2H, m), 4.08–4.19(1H, m), 4.41(2H, s), 5.46(2H, s), 6.77(2H, s), 7.17(1H, dd, J=4.5, 7.4), 7.18–7.29(5H, m), 8.27(1H, d, J=7.4), 8.49(1H, d, J=4.5) |
| 6 | 3.16(3H, s), 3.59–3.80(2H, m), 3.87–3.97(1H, m), 4.18–4.29(1H, m), 4.58(2H, s), 5.45(2H, s), 7.08–7.24(6H, m), 7.95–8.05(3H, m), 8.27(1H, d, J=7.9), 8.49(1H, d, J=4.6) |
| 7 | 3.12(3H, s), 3.45–3.58(1H, m), 3.65–3.79(2H, m), 4.10–4.19(1H, m), 4.32(2H, s), 5.47(2H, s), 5.94(2H, d, J=7.9), 6.74(2H, s), 6.87(1H, s), 7.10–7.24(6H, m), 8.29(1H, d, J=7.4), 8.49(1H, d, J=4.5) |

TABLE 8

| Example No. | $^1$H-NMR(δ: ppm) |
|---|---|
| 8 | 3.12(3H, s), 3.45–3.60(1H, m), 3.65–3.77(2H, m), 3.78(3H, s), 4.11–4.20(1H, m), 4.32(2H, s), 5.47(2H, s), 5.91(2H, d, J=6.4), 6.54(1H, s), 6.60(1H, s), 7.12–7.23(6H, m), 8.26(1H, d, J=7.9), 8.48(1H, d, J=4.5) |
| 9 | 3.13(3H, s), 3.50–3.61(1H, m), 3.62(3H, s), 3.72(3H, s), 3.73–3.84(2H, m), 4.07–4.18(1H, m), 4.30(2H, s), 5.48(2H, s), 6.42(1H, s), 6.45(1H, s), 7.17(1H, dd, J=4.9, 7.9), 7.18–7.26(5H, m), 8.29(1H, d, J=7.9), 8.49(1H, d, J=4.9) |
| 10 | 3.12(3H, s), 3.47–3.61(1H, m), 3.71(3H, s), 3.75–3.82(2H, m), 4.08–4.17(1H, m), 4.31(2H, s), 5.48(2H, s), 6.58(2H, s), 7.17(1H, dd, J=4.5, 7.6), 7.18–7.27(5H, m), 8.25(1H, d, J=7.9), 8.49(1H, d, J=4.5) |
| 11 | 3.16(3H, s), 3.84–3.96(1H, m), 4.07–4.18(1H, m), 4.31–4.43(2H, m), 6.90–6.99(3H, m), 7.09(1H, dd, J=4.7, 7.9), 7.23–7.33(1H, m), 8.14(1H, d, J=7.9), 8.41(1H, d, J=4.7), 10.84(1H, brs) |
| 12 | 3.20(3H, s), 3.85–3.96(1H, m), 4.08–4.19(1H, m), 4.31–4.44(2H, m), 5.45(2H, s), 6.87–6.97(3H, m), 7.18–7.29(8H, m), 8.27(1H, d, J=7.4), 8.48(1H, d, J=4.5) |
| 13 | 3.10(3H, s), 3.45(3H, s), 3.55(3H, s), 3.80–3.90(1H, m), 4.10–4.21(1H, m), 4.30–4.41(2H, m), 5.35(2H, s), 6.09(2H, s), 7.11–7.24(6H, m), 8.27(1H, d, J=7.4), 8.48(1H, d, J=4.9) |
| 14 | 3.18(3H, s), 3.56(3H, s), 3.70(9H, s), 3.80–3.94(1H, m), 4.09–4.18(1H, m), 4.31–4.45(2H, m), 5.45(2H, s), 6.19(2H, s), 6.83(2H, d, J=8.9), 7.12–7.20(3H, m), 8.27(1H, d, J=7.6), 8.48(1H, d, J=4.6) |

TABLE 9

| Example No. | $^1$H-NMR(δ: ppm) |
|---|---|
| 15 | 3.20(3H, s), 3.55(3H, s), 3.57(6H, s), 3.61(6H, s), 3.64(6H, s), 3.79–3.91(1H, m), 4.11–4.20(1H, m), 4.32–4.46(2H, m), 5.40(2H, s), 6.18(2H, s), 6.59(2H, s), 7.17(1H, dd, J=4.5, 7.4), 8.27(1H, d, J=7.4), 8.53(1H, d, J=4.5) |
| 16 | 2.45(3H, s), 3.18(3H, s), 3.55(3H, s), 3.65(6H, s), 3.80–3.94(1H, m), 4.08–4.18(1H, m), 4.30–4.43(2H, m), 5.43(2H, s), 6.18(2H, s), 7.02(1H, d, J=7.9), 7.13–7.29(5H, m), 8.13(1H, d, J=7.9) |

TABLE 9-continued

| Example No. | $^1$H-NMR(δ: ppm) |
|---|---|
| 17 | 3.16(3H, s), 3.76(3H, s), 3.79(3H, s), 3.83–3.95(1H, m), 4.15–4.23(1H, m), 4.30–4.49(2H, m), 7.01(2H, d, J=8.9), 7.08(1H, dd, J=4.5, 7.4), 7.42(2H, d, J=8.9), 7.68(1H, s), 8.11(1H, d, J=7.4), 8.41(1H, d, J=4.5), 10.84(1H, brs) |
| 18 | 3.00(2H, d, J=7.9), 3.15(3H, s), 3.59(6H, s), 3.77–3.94(1H, m), 4.02–4.15(1H, m), 4.25–4.37(1H, m), 6.83(2H, d, J=8.9), 7.05–7.15(3H, m), 7.42(2H, d, J=8.9), 8.13(1H, d, J=7.9), 8.41(1H, d, J=4.9), 10.83(1H, brs) |
| 19 | 3.21(3H, s), 3.77(3H, s), 3.79(3H, s), 3.82–3.95(1H, m), 4.15–4.27(1H, m), 4.34–4.51(2H, m), 5.43(2H, s), 6.97(2H, d, J=8.9), 7.10–7.19(6H, m), 7.40(2H, d, J=8.9), 7.67(1H, s), 8.25(1H, d, J=7.4), 8.48(1H, d, J=4.8) |
| 20 | 3.00(2H, d, J=8.1), 3.19(3H, s), 3.59(6H, s), 3.75–3.82(1H, m), 3.83–3.94(1H, m), 4.05–4.17(1H, m), 4.27–4.40(2H, m), 5.45(2H, s), 6.80(2H, d, J=8.1), 7.07(2H, d, J=8.1), 7.11–7.24(6H, m), 8.26(1H, d, J=7.4), 8.47(1H, d, J=4.8) |

TABLE 10

| Example No. | $^1$H-NMR(δ: ppm) |
|---|---|
| 21 | 1.93–2.10(2H, m), 3.17(3H, s), 4.04(2H, t, J=6.3), 4.06–4.17(1H, m), 5.46(2H, s), 6.83–6.92(3H, m), 7.16(1H, dd, J=4.6, 7.6), 7.17–7.28(7H, m), 8.27(1H, d, J=7.6), 8.49(1H, d, J=4.6) |
| 22 | 1.92–2.08(2H, m), 3.14(3H, s), 3.39–3.55(1H, m), 3.56(3H, s), 3.73(6H, s), 3.96–4.15(3H, m), 6.21(2H, s), 7.09(1H, dd, J=4.5, 7.9), 8.15(1H, d, J=7.9), 8.41(1H, d, J=4.5), 10.91(1H, brs) |
| 23 | 0.88(3H, t, J=7.4), 1.50–1.69(2H, m), 1.91–2.08(2H, m), 3.16(3H, s), 3.40–3.54(1H, m), 3.56(3H, s), 3.71(6H, s), 4.01(2H, t, J=5.9), 4.08–4.22(3H, m), 6.18(2H, s), 7.15(1H, dd, J=4.5, 7.9), 8.26(1H, d, J=7.9), 8.54(1H, d, J=4.5) |
| 24 | 1.94–2.07(2H, m), 2.45(3H, s), 3.16(3H, s), 3.40–3.55(1H, m), 3.56(3H, s), 3.70(6H, s), 3.97–4.05(2H, m), 4.06–4.19(1H, m), 5.43(2H, s), 6.18(2H, s), 7.02(1H, d, J=7.9), 7.13–7.31(6H, m), 8.14(1H, d, J=7.9) |
| 25 | 1.93–2.08(2H, m), 3.17(3H, s), 3.43–3.54(1H, m), 3.56(3H, s), 3.66(3H, s), 3.70(6H, s), 3.95–4.03(2H, m), 4.04–4.20(1H, m), 5.37(2H, s), 6.19(2H, s), 6.78(2H, d, J=8.6), 7.16(1H, dd, J=4.5, 7.6), 7.21(2H, d, J=8.6), 8.27(1H, d, J=7.6), 8.50(1H, d, J=4.6) |
| 26 | 1.91–2.09(2H, m), 3.18(3H, s), 3.40–3.55(1H, m), 3.56(3H, s), 3.65(3H, s), 3.70(6H, s), 3.97–4.08(2H, m), 4.09–4.22(1H, m), 5.40(2H, s), 6.19(2H, s), 6.58(2H, s), 7.17(1H, dd, J=4.5, 7.9), 8.28(1H, d, J=7.9), 8.52(1H, d, J=4.5) |

TABLE 11

| Example No. | $^1$H-NMR(δ: ppm) |
|---|---|
| 27 | 1.10–1.83(8H, m), 2.52–2.75(2H, m), 3.61(6H, s), 3.75–3.90(6H, m), 4.10–4.21(2H, m), 4.35(4H, s), 5.23–5.47(1H, m), 6.62(4H, s), 7.15(1H, dd, J=4.7, 7.7), 8.25(1H, d, J=7.7), 8.53(1H, d, J=4.7) |
| 28 | 3.60(6H, s), 3.67(12H, m), 3.68–3.89(6H, m), 4.10–4.20(2H, m), 4.37(4H, s), 6.61(4H, s), 7.10–7.18(3H, m), 7.37–7.49(3H, m), 8.25–8.37(2H, m) |
| 29 | 3.16(3H, s), 3.55(3H, s), 3.70(6H, s), 3.71–3.88(1H, m), 4.06–4.18(1H, m), 4.28–4.45(2H, m), 6.22(2H, s), 7.10(1H, dd, J=4.7, 7.7), 8.14(1H, d, J=7.7), 8.40(1H, d, J=4.7), 10.85(1H, brs) |
| 30 | 1.75–1.93(2H, m), 3.12(3H, s), 3.40–3.55(3H, m), 3.63(3H, s), 3.76(6H, s), 3.90–4.05(1H, m), 4.36(2H, s), 6.61(2H, s), |

TABLE 11-continued

| Example No. | $^1$H-NMR($\delta$: ppm) |
|---|---|
|  | 7.09(1H, dd, J=4.9, 7.9), 8.13(1H, d, J=7.9), 8.41(1H, d, J=4.9), 10.84(1H, brs) |
| 31 | 3.61(3H, s), 3.65–3.90(8H, m), 4.25–4.35(1H, m), 4.41(2H, s), 4.65–4.75(1H, m), 6.63(2H, s), 7.12(1H, dd, J=4.7, 7.7), 7.51–7.61(3H, m), 7.81–7.90(2H, m), 8.17(1H, d, J=7.7), 8.45(1H, d, J=4.7), 11.00(1H, brs) |
| 32 | 1.18(3H, t, J=7.4), 1.91–2.08(2H, m), 3.30–3.50(2H, m), 3.56(3H, s), 3.72(6H, s), 3.95–4.15(4H, m), 6.20(2H, s), 7.09(1H, dd, J=4.9, 7.9), 8.13(1H, d, J=7.9), 8.41(1H, d, J=4.9), 10.85(1H, brs) |

TABLE 12

| Example No. | $^1$H-NMR($\delta$: ppm) |
|---|---|
| 33 | 3.54(3H, s), 3.68(3H, s), 3.77–3.86(1H, m), 4.05–4.17(1H, m), 4.33–4.40(1H, m), 4.48–4.57(1H, m), 4.76(1H, d, J=12.0), 5.39(1H, d, J=12.0), 6.20(2H, s), 7.08(1H, dd, J=4.4, 7.2), 8.11(1H, d, J=7.2), 8.40(1H, d, J=4.4) |
| 34 | 1.20(3H, t, J=7.4), 1.95–2.11(2H, m), 3.35–3.52(2H, m), 3.56(3H, s), 3.69(6H, s), 3.95–4.05(3H, m), 4.05–4.20(1H, m), 5.46(2H, s), 6.18(2H, s), 7.11–7.26(6H, m), 8.27(1H, d, J=7.9), 8.48(1H, d, J=5.0) |
| 35 | 1.97–2.17(2H, m), 3.56(3H, s), 3.57–3.68(1H, m), 3.69(6H, s), 4.03(2H, t, J=6.4), 4.21–4.35(1H, m), 4.75(1H, d, J=11.4), 5.33–5.43(3H, m), 6.17(2H, s), 7.03–7.35(1H, m), 8.23(1H, d, J=7.4), 8.44(1H, d, J=5.0) |
| 36 | 3.17(3H, s), 3.50(3H, s), 3.55(3H, s), 3.69(6H, s), 3.80–3.88(1H, s), 4.10–4.18(1H, m), 4.31–4.42(2H, m), 6.20(2H, s), 7.17(1H, dd, J=4.8, 7.6), 8.25(1H, d, J=7.6), 8.55(1H, d, J=4.8) |
| 37 | 1.12(3H, t, J=6.8), 3.18(3H, s), 3.54(3H, s), 3.68(6H, s), 3.80–3.89(1H, m), 4.08–4.18(1H, m), 4.27(2H, q, J=6.8), 4.30–4.41(2H, m), 6.19(2H, s), 7.16(1H, dd, J=4.8, 7.6), 8.25(1H, d, J=7.6), 8.55(1H, d, J=4.8) |
| 38 | 1.91–2.13(2H, m), 3.47–3.50(1H, m), 3.54(3H, s), 3.72(6H, s), 4.02(2H, t, J=5.6), 4.74(1H, d, J=11.6), 5.39(1H, d, J=11.6), 6.19(2H, s), 7.07(1H, dd, J=4.4, 7.6), 7.31(5H, s), 8.11(1H, d, J=7.6), 8.39(1H, d, J=4.4), 10.80(1H, brs) |

Pharmacological Test 1

Therapeutic Effect on Diabetic Neuropathy

A model group was obtained by intravenously administering 50 mg/kg streptozotocin (STZ) dissolved in 0.01 M citrate buffer solution to 8-week-old male S.D. rats. After administration, five rats were housed per cage and kept therein.

Three weeks after administration of STZ, the pain threshold of each rat's left hind paw to pressure stimulation was measured by Randall-Selitto Test [Randall, L. O. and Selitto, J. J. Arch. Int. Pharmacodyn., 111, 409–419 (1957)]. The value thus obtained was termed "pre-value".

Rats exhibiting a pre-value of 30 mmHg or less were chosen and divided into three groups so that each group had 8–10 rats (n=8–10).

A 5% gum arabic solution containing the test compound was orally administered as specimen to experimental animals in one of the above three groups (test group) in such a manner that each dosage of the test compound was 30 mg/kg and the amount of administered solution was 10 ml/kg, once a day for 21 continuous days. Another group was defined as the control group, and only a 5% gum arabic solution was administered as specimen to experimental animals in the control group in such a manner that each dosage was 10 ml/kg, once a day for 21 continuous days. Finally, in the third group no specimen was administered to the experimental animals (non-treated group).

On the 14$^{th}$ and 21$^{st}$ days, the pain threshold of the left hind paw of the experiment animals was measured three hours after administration. The recovery rate (%) of the pain threshold was calculated by means of the following formula:

Recovery rate (%)=[(T−C)/(N−C)]×100

(wherein T is the test group average value, C is the control group average value and N is the non-treated group average value.)

Table 13 below shows the results.

TABLE 13

| | Recovery rate (%) | |
|---|---|---|
| Test compound | 14$^{th}$ day | 21$^{st}$ day |
| Example 1 | 46.2 | 56.7 |

As is clear from the results shown in Table 13, the compound of the present invention exhibits excellent effects in treating diabetic neuropathy.

Pharmacological Test 2

Adenosine Enhancing Effect

The compounds obtained in Examples 1 and 34 were used as test compounds in the form of a dimethyl sulfoxide solution.

As experimental animals, Hartley male guinea pigs (purchased from CHARLES RIVER JAPAN, INC.) (that were in good general condition at least 6 days after the purchase) were used. The animals were housed in a cage under controlled conditions of temperature of 20 to 26° C. (actually measured value: 22.1 to 22.9° C.), humidity of 40–70% (actually measured value: 50.3–51.5%) and lighting of 12 hours/day (7:00–19:00). The animals had free access to food (solid diet, product name of Labo G Standard, product of Nosan Corporation) and tap water.

The following experiments were conducted using the excised ilea (n=2) of experimental animals (body weight at the time of testing: 316–388 g). The experimental animals were bled and slaughtered. The ileum thereof was extracted and suspended under a tension of 0.5 g in a bath (organ bath) filled with a nutrient solution (Krebs-Henseleit solution; amount=10 mL, solution temperature=32° C.) gassed with a mixed gas of 95% oxygen+5% carbon dioxide. Contraction by transmural electrical stimulation was induced using an electronic stimulator (product of NIHON KOHDEN CORPORATION, SEN-3301) and 4 channel bus drive amplifier (product of NIHON KOHDEN CORPORATION, SEG-3104) by applying rectangular wave electronic stimulation (frequency: 0.1 Hz, duration: 5 msec, voltage: sub-maximum voltage (V)) via ring-shaped platinum electrodes. The contraction reaction of samples was recorded on an ink-writing recorder (GRAPHTEC, SR-6211, SR-6221) through an isotonic transducer (product of NIHON KOHDEN CORPORATION, TD-112S).

While exchanging the nutrient solution about every 20 minutes, the samples were left in the nutrient solution for 30–60 minutes, and then electric stimulation was applied thereto. After the contraction reaction stabilized, $10^{-6}$ M to $10^{-5}$ M of adenosine (product of Wako Pure Chemical Industries, Ltd) was cumulatively added thereto, and reduction of contraction reaction was monitored as below.

That is, the nutrient solution was exchanged, electronic stimulation was applied to the samples 15 minutes after exchange of the nutrient solution, and, when contraction stabilized, adenosine was cumulatively added from $10^{-6}$ M to $10^{-5}$ M. The adenosine dose-response curve was then obtained, and the $ED_{50}$ value was calculated.

The nutrient solution was then exchanged and electronic stimulation was again applied to the samples 15 minutes later. When the contraction stabilized, test compounds having a final concentration of $10^{-7}$ M, $10^{-6}$ M and $10 M^{-5}$ were added thereto and reacted for 5 minutes. Thereafter, adenosine was cumulatively added from $10^{-6}$ M to $10^{-5}$ M, and the adenosine dose-response curve was then obtained and the $ED_{50}$ value [$ED_{50}(+)$] of adenosine in the presence of the test compound was calculated.

The adenosine enhancement effect was then determined as the ratio of the $ED_{50}$ value in the absence of the test compound [$ED_{50}(-)$], i.e., ($ED_{50}(-)/ED_{50}(+)$).

The obtained results were shown in Table 14 below.

TABLE 14

| Test compound | Concentration (M) | Adenosine enhancing effect ($ED_{50}(-)/ED_{50}(+)$) |
|---|---|---|
| Example 1 | $10^{-6}$ | 11.11 |
| Example 34 | $10^{-5}$ | 14.00 |

As seen from the results shown in Table 14, it is clear that the compounds of the present invention exhibit excellent adenosine enhancing effects.

Pharmacological Test 3

Test for Evaluating Analgesic Effect

Using two groups (test group and control group) each consisting of 6-week-old male S.D. rats (7 rats in each group), the pain threshold of each rat's left hind paw was measured using an Analgesy-meter (product of Unicom) in accordance with the Randall-Sellitto method [Randall, L. O. and Sellitto, J. J., Arch. Int. Pharmacodyn., 111, 409–419 (1957)]. The value thus obtained was termed "pre-value".

One hour after the measurement of the pre-value, a 5% gum arabic suspension containing compound of the invention was orally administered to the rats of the test group in an amount of 10 ml/kg, whereas a 5% gum arabic suspension (not containing compound of the invention) was orally administered to the rats of the control group in an amount of 10 ml/kg.

One hour after the oral administration, a physiological saline solution containing Substance P (25 ng/0.1 ml) was subcutaneously injected into the left hind paw of each rat.

The pain threshold of each rat's left hind paw was measured in the same manner as above at predetermined time intervals after the Substance P injection. The measured value is termed the "post-value".

The recovery rate (%) of the pain threshold was calculated from the post-values and pre-values of the test group and control group, by means of the following formula:

$$\text{Recovery rate of pain threshold (\%)} = \frac{[(\text{test group average post value}) - (\text{control group average post-value})]}{[(\text{control group average pre-value}) - (\text{control group average post-value})]} \times 100$$

Table 15 shows the results (highest recovery rate).

TABLE 15

| Test compound | Recovery rate (%) | Measurement point (minutes after injection) |
|---|---|---|
| Example 1 | 46 | 60 |
| Example 15 | 39 | 60 |
| Example 36 | 111 | 60 |

From the results shown in Table 15, it is clear that the compounds obtained in Examples 1, 15 and 36 of the invention exhibit an excellent analgesic effect.

Furthermore, the compounds shown in Tables 16 and 17 below can also be produced in the same manner as in the above-described Examples. These compounds belong to group (8) of the invention described above. When these compounds are subjected to the tests as described in the above Pharmaceutical Tests, they are considered to achieve substantially the same results as shown in Tables 13–15.

TABLE 16

Compound 101                                      Compound 102

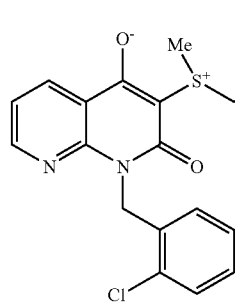
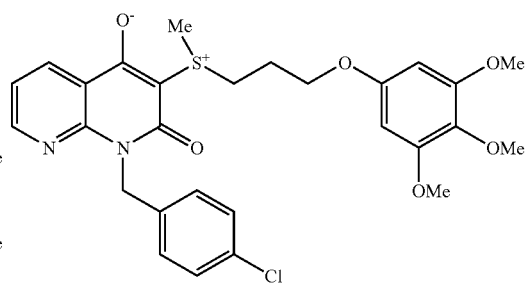

TABLE 16-continued
Compound 103
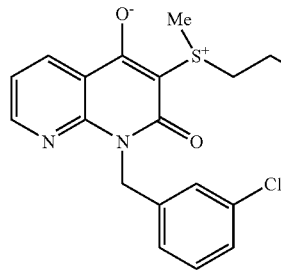
Compound 104
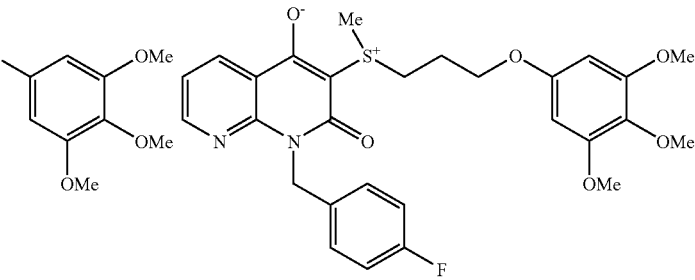
Compound 105
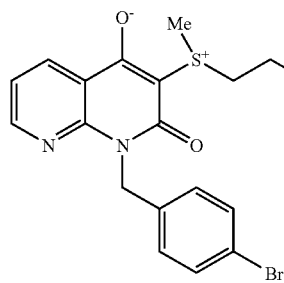
Compound 106
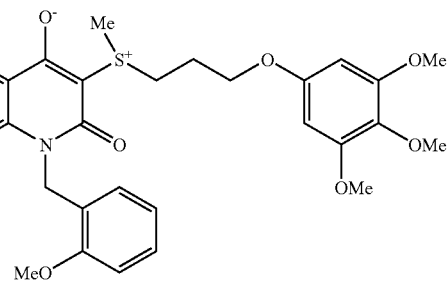
Compound 107
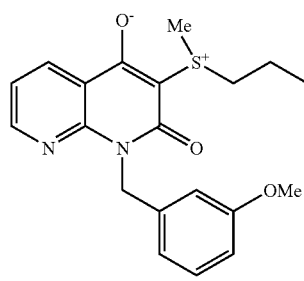
Compound 108
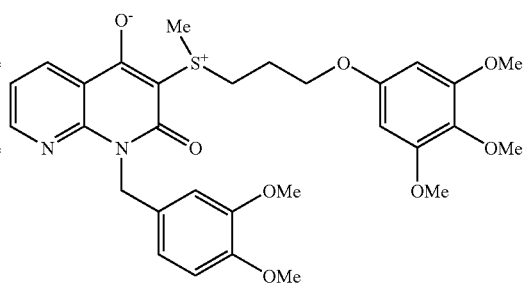
Compound 109
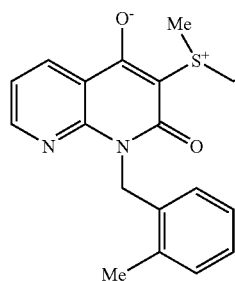
Compound 110
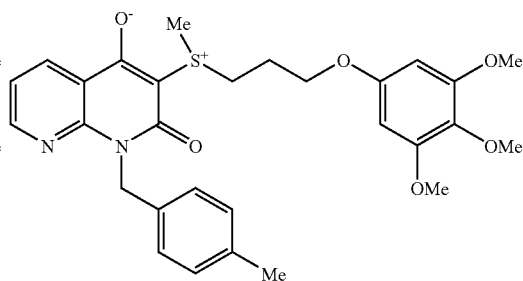

TABLE 16-continued
Compound 111
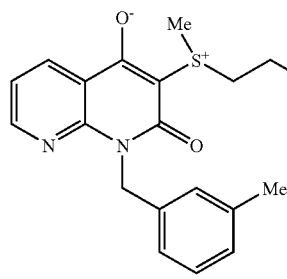
Compound 112
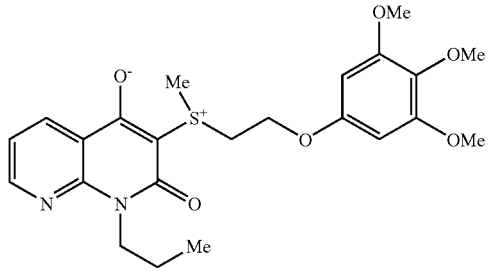
Compound 113
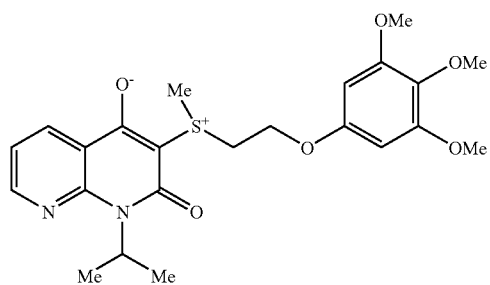
Compound 114
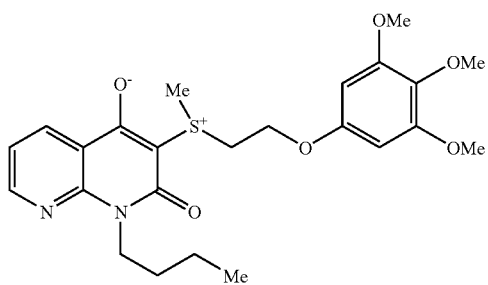
Compound 115
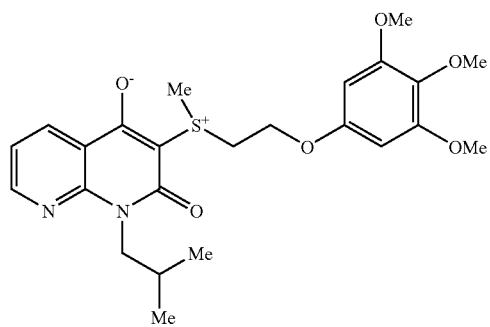
TABLE 17
Compound 116
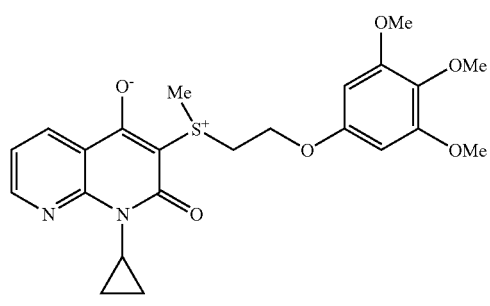
Compound 117
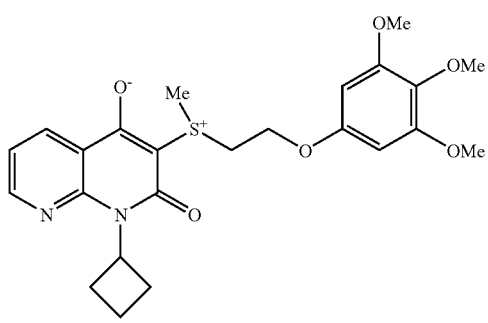

TABLE 17-continued

Compound 118

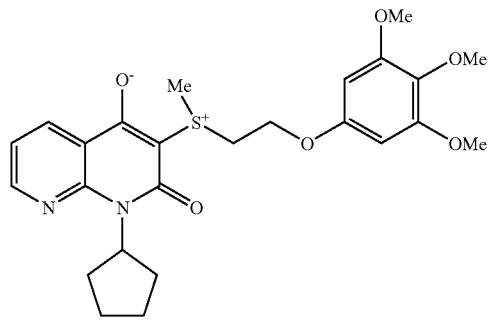

Compound 119

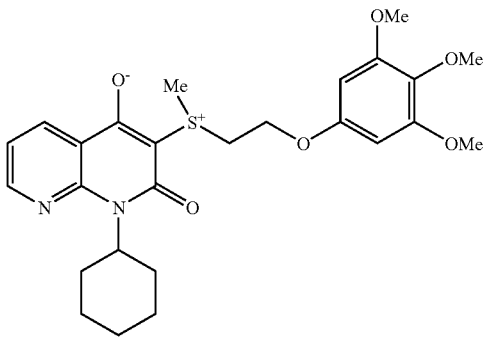

Compound 120

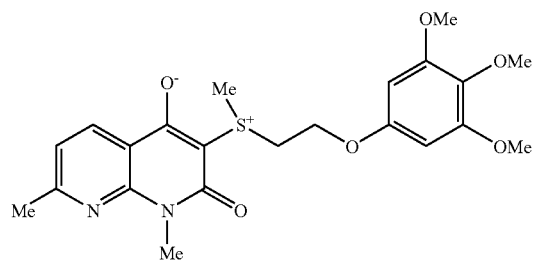

Compound 121

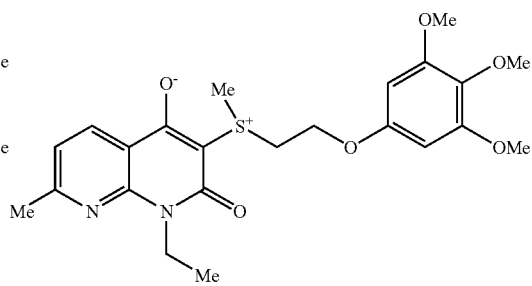

Compound 122

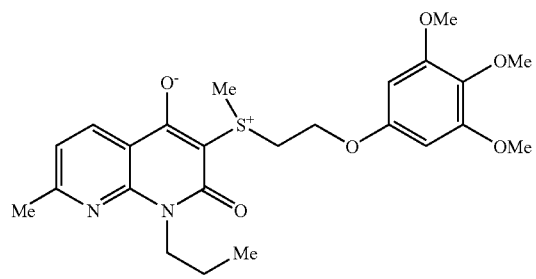

Formulation Example 1

Tablets (2000 tables), each containing as an active ingredient 300 mg of the compound of the invention obtained in Example 1, were manufactured according to the following formulation:

| | |
|---|---|
| Compound of the invention obtained in Example 1 | 600 g |
| Lactose (Japanese pharmacopoeia) | 67 g |
| Corn starch (Japanese pharmacopoeia) | 33 g |
| Carboxymethyl cellulose calcium (Japanese pharmacopoeia) | 25 g |
| Methyl cellulose (Japanese pharmacopoeia) | 12 g |
| Magnesium stearate (Japanese pharmacopoeia) | 3 g |

More specifically, the compound of the invention obtained in Example 1, lactose, corn starch and carboxymethyl cellulose calcium were well blended and granulated using an aqueous methyl cellulose solution. The granulated mixture was passed through a 24-mesh sieve, and the granules under the sieve were mixed with magnesium stearate and compression-molded to give the desired tablets.

Formulation Example 2

Hard gelatin capsules (2000 capsules), each containing as an active ingredient 200 mg of the compound of the invention obtained in Example 25, were manufactured according to the following formulation:

| | |
|---|---|
| Compound of the invention obtained in Example 25 | 400 g |
| Crystalline cellulose (Japanese pharmacopoeia) | 60 g |
| Corn starch (Japanese pharmacopoeia) | 34 g |
| Talc (Japanese pharmacopoeia) | 4 g |
| Magnesium stearate (Japanese pharmacopoeia) | 2 g |

More specifically, the above ingredients were finely pulverized and blended to give a homogeneous mixture. This mixture was placed in appropriately sized gelatin capsule shells for oral administration to provide the desired capsules.

The invention claimed is:

1. A naphthyridine compound represented by the following general formula (1):

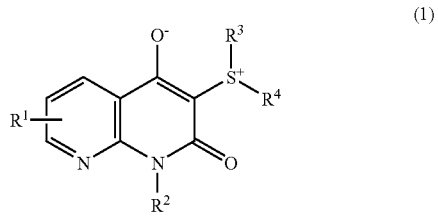

wherein $R^1$ represents a hydrogen atom or a lower alkyl group;

$R^2$ represents a hydrogen atom, a lower alkyl group, a cycloalkyl group, phenyl group, or a phenyl-lower alkyl group optionally having 1 to 3 lower alkoxy groups on the phenyl ring;

$R^3$ and $R^4$ each independently represent the group —Y—O—Z—$R^5$ (wherein Y is a lower alkylene group, Z is a single bond or a lower alkylene group, and $R^5$ is phenyl group optionally having 1 to 3 substituents selected from the group consisting of halogen atoms, lower alkoxy groups, lower alkyl groups, halogen-substituted lower alkyl groups, methylenedioxy group, hydroxyl group, 2,2-di(lower alkoxy-carbonyl)ethyl groups and 2,2-di(lower alkoxy-carbonyl)vinyl groups, or one of $R^3$ and $R^4$ is the group —Y—O—Z—$R^5$ (wherein Y, Z and $R^5$ are as above) and the other is a lower alkyl group, phenyl group, or a phenyl-lower alkyl group;

with the proviso that the case where $R^2$ is a phenyl-lower alkyl group optionally having 1 to 3 lower alkoxy groups on the phenyl ring and at least one of $R^3$ and $R^4$ is a benzyloxy-lower alkyl group having 1 to 3 lower alkoxy groups on the benzene ring is excluded.

2. A naphthyridine compound according to claim 1, wherein one of $R^3$ and $R^4$ is a lower alkyl group.

3. A naphthyridine compound according to claim 1, wherein $R^1$ is a hydrogen atom and either $R^3$ or $R^4$ is a lower alkyl group.

4. A naphthyridine compound according to claim 1, wherein $R^1$ is a hydrogen atom, $R^2$ is a phenyl-lower alkyl group optionally having 1 to 3 lower alkoxy groups on the phenyl ring and either $R^3$ or $R^4$ is a lower alkyl group.

5. A naphthyridine compound according claim 1, wherein $R^1$ is a hydrogen atom, $R^2$ is a phenyl-lower alkyl group optionally having 1 to 3 lower alkoxy groups on the phenyl ring, one of $R^3$ and $R^4$ is a lower alkyl group and Z is a single bond.

6. A naphthyridine compound according to claim 1, wherein $R^1$ is a hydrogen atom, $R^2$ is a phenyl-lower alkyl group optionally having 1 to 3 lower alkoxy groups on the phenyl ring, one of $R^3$ and $R^4$ is a lower alkyl group, $R^5$ is phenyl group having 1 to 3 lower alkoxy groups as substituents and Z is a single bond.

7. A naphthyridine compound according to claim 1, wherein $R^1$ is a hydrogen atom, $R^2$ is benzyl optionally substituted with 1 to 3 lower alkoxy groups on the phenyl ring, one of $R^3$ and $R^4$ is a lower alkyl group, $R^5$ is phenyl group having 1 to 3 lower alkoxy groups as substituents and Z is a single bond.

8. A naphthyridine compound according to claim 1, wherein one of $R^3$ and $R^4$ is a lower alkyl group and Z is a single bond.

9. A naphthyridine compound according to claim 1, wherein one of $R^3$ and $R^4$ is a lower alkyl group, $R^5$ is phenyl group having 3 lower alkoxy groups as substituents and Z is a single bond.

10. A naphthyridine compound according to claim 1, wherein one of $R^3$ and $R^4$ is a lower alkyl group, $R^5$ is a 3,4,5-tri-lower alkoxy-phenyl group and Z is a single bond.

11. A naphthyridine compound according to claim 1, which is selected from the group consisting of 1-(3,4,5-trimethoxybenzyl)-3-[methyl-2-(3,4,5-trimethoxyphenoxy)ethylsulfonium]-1,8-naphthyridine-2(1H)-one-4-olate, 1-benzyl-3-[ethyl-3-(3,4,5-trimethoxyphenoxy)propylsulfonium]-1,8-naphthyridine-2(1H)-one-4-olate, 1-methyl-3-[methyl-2-(3,4,5-trimethoxyphenoxy)ethylsulfonium]-1,8-naphthyridine-2(1H)-one-4-olate, 1-benzyl-3-[methyl-3-(3,4,5-trimethoxyphenoxy)propylsulfonium]-1,8-naphthyridine-2(1H)-one-4-olate, and 1-(4-methoxybenzyl)-3-[methyl-3-(3,4,5-trimethoxyphenoxy)propylsulfonium]-1,8-naphthyridine-2(1H)-one-4-olate.

12. A naphthyridine compound according to claim 1, which is 1-benzyl-3-[methyl-3-(3,4,5-trimethoxyphenoxy)propylsulfonium]-1,8-naphthyridine-2(1H)-one-4-olate.

13. A pharmaceutical composition comprising a therapeutically or pharmaceutically effective amount of a naphthyridine compound of claim 1 together with an inert pharmaceutically acceptable carrier.

14. A pharmaceutical composition according to claim 13, which is an analgesic.

15. A pharmaceutical composition according to claim 13, which is a diabetic neuropathy treating agent.

16. A pharmaceutical composition according to claim 13, which is an adenosine enhancement agent.

17. A method for relieving pain comprising administering an effective amount of a naphthyridine compound of claim 1 to a patient in need of treatment.

18. A method for treating diabetic neuropathy comprising administering an effective amount of a naphthyridine compound of claim 1 to a patient in need of treatment.

* * * * *